US006605727B2

(12) United States Patent
Wood et al.

(10) Patent No.: US 6,605,727 B2
(45) Date of Patent: *Aug. 12, 2003

(54) PROCESSES FOR THE PREPARATION OF BENZOTRIAZOLE UV ABSORBERS

(75) Inventors: Mervin G. Wood, Poughquag, NY (US); Deborah DeHessa, Poughkeepsie, NY (US); Joseph Suhadolnik, Yorktown Heights, NY (US); Andrew B. Naughton, Mobile, AL (US); Jerome Sanders, Mobile, AL (US); Jacqueline Lau, Jericho, NY (US); Rong Xiong, Dobbs Ferry, NY (US); Joseph Babiarz, Amawalk, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/315,692

(22) Filed: Dec. 10, 2002

(65) Prior Publication Data

US 2003/0120083 A1 Jun. 26, 2003

Related U.S. Application Data

(60) Division of application No. 09/871,369, filed on May 31, 2001, which is a continuation-in-part of application No. 09/632,217, filed on Aug. 3, 2000, now Pat. No. 6,353,113.

(51) Int. Cl.$^7$ .................. C07D 249/20; C07D 413/10; C07D 403/10; C07D 401/10
(52) U.S. Cl. ................. 548/260; 546/199; 544/136; 544/366
(58) Field of Search .......... 548/260; 546/199, 546/136, 366

(56) References Cited

U.S. PATENT DOCUMENTS

| 2,418,416 A | 4/1947 | Locke | 260/195 |
|---|---|---|---|
| 2,478,767 A | 8/1949 | Locke | 260/144 |
| 2,478,768 A | 8/1949 | Locke | 260/144 |
| 3,793,305 A | 2/1974 | Balon | 260/154 |
| 4,035,350 A | 7/1977 | Landler et al. | 260/152 |
| 4,141,903 A | 2/1979 | Adler | 260/308 |
| 5,436,322 A | 7/1995 | Orban et al. | 534/581 |
| 5,977,219 A | 11/1999 | Ravichandran | 524/91 |
| 6,262,151 B1 | 7/2001 | Ravichandran et al. | 524/89 |
| 6,353,113 B1 * | 3/2002 | Wood et al. | 548/260 |

FOREIGN PATENT DOCUMENTS

| DE | 116230 | 11/1961 |
|---|---|---|
| DE | 3731860 | 11/1988 |
| EP | 0751134 | 1/1997 |
| EP | 0794179 | 9/1997 |
| GB | 2319035 | 5/1998 |
| JP | 357690 | 3/1991 |

OTHER PUBLICATIONS

J. Org. Chem. (1985), vol. 50, No. 19, pp. 3612–3614.
Y. Hashida et al., Bull. Chem. Soc. Jpn., vol. 61, pp. 905–909, (1988).
S. Tamagaki et al., Chemistry Letters, pp. 1237–1240, (1982).
J. March, Advanced Organic Chemistry, Reactions, Mechanisms and Structure, 4$^{th}$ Ed., pp. 522–523 (1964).
English Abstract for DE 3731860 (1988).
R. Trimmer et al., Journal of Organic Chemistry, vol. 50, No. 19, (1985), pp. 3612–3614.
Chemical Abstract 114:207270f (1991) for JP 0302172.
Chemical Abstract 123:32443w (1995) for M. V. Gorelik et al., Research Institute Organic Intermediates Dyes, Moscow, Russia 103787, Mendeleev Commun. 1995, (2), pp. 64–65.
Chemical Abstract 91:108994v (1979) for JP 7932423.

\* cited by examiner

*Primary Examiner*—Patricia L. Morris
(74) *Attorney, Agent, or Firm*—Tyler A. Stevenson

(57) ABSTRACT

Provided is a process for preparing 2H-benzotriazole UV absorbers containing a perfluoroalkyl moiety at the 5-position of the benzo ring, for example a trifluoromethyl group, which involves diazotizing the perfluoroalkyl substituted o-nitroaniline using concentrated sulfuric acid plus sodium nitrite or nitrosylsulfuric acid to form the corresponding monoazobenzene intermediate via the diazonium salt intermediate which is reduced to the corresponding 5-perfluoroalkyl substituted 2H-benzotriazole UV absorber compound by conventional reduction means. Also provided is a novel one-pot, multiphase reaction for the preparation of 2(2-nitrophenylazo) substituted phenols, which are precursors for 2H-benzotriazole UV absorbers.

28 Claims, No Drawings

PROCESSES FOR THE PREPARATION OF BENZOTRIAZOLE UV ABSORBERS

This is a divisional of application Ser. No. 09/871,369, filed May 31, 2001, which is a continuation-in-part of application Ser. No. 09/632,217, filed Aug. 3, 2000, now U.S. Pat. No. 6,353,113, issued Mar. 5, 2002.

The instant invention pertains to a superior process for making 2H-benzotriazole UV absorbers which are substituted by a perfluoroalkyl group, i.e. trifluoromethyl, usually at the 5-position of the benzo ring; and to a novel process for the preparation of the intermediate 2-(2-nitophenylazo) phenols.

BACKGROUND OF THE INVENTION

Japanese TOKU-KAI-Hei 3-57690 generically discloses compounds where the benzo ring of the benzotriazole may be substituted by a host of groups including hydrogen, alkyl, alkoxy, aryloxy, halogen, substituted amino, cyano, nitro, acyl and trihalomethyl. The only specific benzotriazole compounds mentioned are those where the benzo ring is unsubstituted or is substituted at the 5-position by a chloro group. There is no evidence that the Japanese inventors made any trihalomethyl substituted benzotriazole.

German Patent Application 116,230 describes inter alia the preparation of 5-trifluoromethyl-2-(2-hydroxy-5-methylphenyl)-2H-benzotriazolyl-1-oxide. The only synthesis conditions disclosed for the entire group of compounds prepared show the diazotization of the appropriate o-nitroaniline with aqueous sodium nitrite and hydrochloric acid. The German workers offer no synthetic details or more importantly no yield information for the preparation of 5-trifluoromethyl-2-(2-hydroxy-5-methylphenyl)-2H-benzotriazolyl-1-oxide.

In British Patent Application 2,319,035 and U.S. Pat. No. 5,977,219, all benzotriazole compounds containing a trifluoromethyl moiety at the 5-position of the benzo ring are referenced to the synthetic procedure of Example 1. Issues to be considered with this synthetic procedure are (a) a 100% excess of the diazonium salt relative to phenol is used; (b) the monoazo prepared by this method is described as a paste (generally materials with the consistency of a paste are impure); the pure monoazo is a solid with a melting point of 101–105° C.; (c) the yield of benzotriazole based on the phenol is 11% and is only 5.5% based on the $CF_3$-substituted o-nitroaniline; (d) the diazotization preparation in Example 1 uses concentrated hydrochloric acid; (e) a paper in the J. Org. Chemistry, 1985, (50) 3612 indicates that the reaction of 4-trifluoromethyl-2-nitroaniline with hydrochloric acid can lead to the formation of 4-trifluoromethyl-2-chloroaniline. Such a reaction could at least partly account for the low yields seen with the use of concentrated hydrochloric acid in the diazotization step.

The following references describe one-pot processes for making azo compounds:

U.S. Pat. No. 2,418,416 describes a process for manufacturing lakes of azo compounds. The process involves dissolving the diazotizable amine and coupling component in an acidic, aqueous solution. The amine was diazotized by addition of the nitrosating reagent to the acidic, aqueous solution. After diazotization was complete, the pH of the solution was raised by addition of base to ca. 7.8.

U.S. Pat. No. 2,478,767 also describes a process for manufacturing lakes of azo compounds. The diazotizable amine is dissolved in an acidic, aqueous solution and heated to 100° F. The coupling component and nitrosating reagent are dissolved in a basic, aqueous solution that is heated to 150° F. The two solutions are mixed together controlling the pH of the mixture in the range of 6–7.2.

U.S. Pat. No. 2,478,768 also describes a process for manufacturing lakes of azo compounds. The process involves adding an acidic, aqueous solution containing a soluble salt of the laking agent to a basic, aqueous solution containing the diazotizable amine, coupling component and nitrosating reagent. The final pH of the reaction mass is 6–7.2.

U.S. Pat. No. 3,793,305 describes a one-step process for the preparation of azo dyes by simultaneously contacting and reacting a diazotizable amine, an active methylene coupling component and a diazotizing agent in an acidic, aqueous solution. The invention requires that the reaction media must be able to dissolve a portion of both the diazotizable amine and the coupling component. The active methylene coupling components named are: b-diketones, b-keto esters, b-keto amides, b-keto nitrites, anilides of cyanoacetic acid, heterocyclic b-keto amides and b-imino amides.

U.S. Pat. No. 4,035,350 describes a process for the preparation of azo dyes where the diazotizable amine and the coupling component are both in solution and the diazotizing agent is added. The invention requires that either the amine or coupling component contain an acid group. The invention also claims the use of polar aprotic solvents that are miscible with water.

Hashida, Y. et. al. reported in "Phase Transfer-Catalyzed Azo Coupling Reaction in Two Phase Systems", Bull. Chem. Soc. Jpn. 61, 905–909 (1988) the phase transfer catalyzed azo coupling reaction in a two phase system. This paper describes the coupling reaction between p-methoxybenzenediazonium tetrafluoroborate with N,N-dimethylaniline in a biphasic water-1,2-dichloroethane system with various phase transfer catalysts.

Tamagaki, S. et. al. reported in Chemistry Letters, pp. 1237–1240 (1982) for the Chemical Society of Japan that silica gel facilitated azo coupling reactions between p nitrobenzenediazonium tetrafluoroborate and aromatic amines. This process involves a solid-solid-liquid multiphase mixture via a solid-liquid interfacial azo-coupling reaction.

In March, J, "Advanced Organic Chemistry," Fourth Ed., New York, pages 522–523, it is pointed out that it is well known that active substrates such as phenols are readily nitrated under standard nitrosation conditions.

OBJECTS OF THE INVENTION

An object of the invention is to provide a facile and improved process for the preparation of 5-perfluoroalkyl substituted 2H-benzotriazole UV absorbers.

Another object of the invention is to provide a novel one-pot process for the preparation of 2-(2-nitrophenylazo) phenols, referred to in this application as monoazobenzene intermediates. These monoazobenzene intermediates are useful for the preparation of hydroxyphenyl benzotriazole UV absorbers.

DETAILED DISCLOSURE

Preparation of 5-Perfluoroalkyl Substituted 2H-Benzotriazoles

The instant invention describes an improved process for the preparation of 5-perfluoroalkyl (for example trifluoromethyl) substituted 2H-benzotriazoles where in the diazotization step aqueous alkali metal (for instance sodium) nitrite and concentrated hydrochloric acid are replaced by aqueous alkali metal (for instance sodium) nitrite and concentrated sulfuric acid; and where aqueous alkali metal (sodium) nitrite and concentrated sulfuric acid are replaced with anhydrous nitrosylsulfuric acid with concentrated sulfuric acid as a diluent to allow operation at safe concentrations.

The instant invention more specifically pertains to a process for preparing a compound of formula (I)

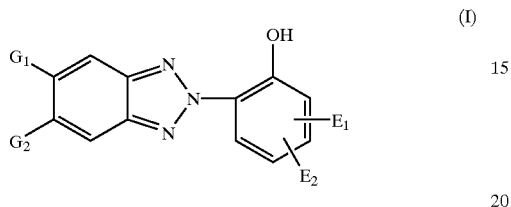

which process comprises
diazotizing a perfluoroalkyl substituted o-nitroaniline of formula (II)

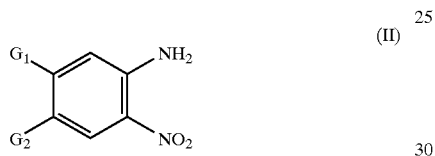

using concentrated sulfuric acid and an alkali metal nitrite (for instance sodium nitrite) or nitrosylsulfuric acid to form the corresponding diazonium salt of formula (III)

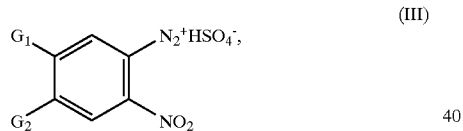

coupling said diazonium salt with a phenol of formula (IV)

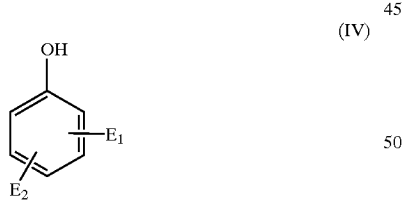

to form a monoazobenzene compound of formula (V)

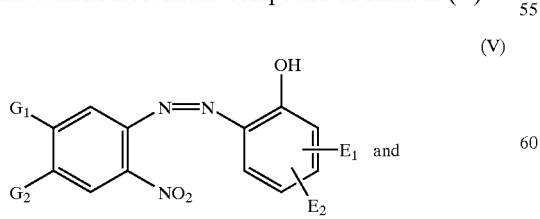

reducing the monoazobenzene intermediate of formula (V) to the corresponding 2H-benzotriazole compound of formula (I) by conventional reduction means;

wherein
$G_1$ is hydrogen or chloro,
$G_2$ is perfluoroalkyl of 1 to 12 carbon atoms,
$E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_1$ is alkyl of 1 to 24 carbon atoms substituted by one or two hydroxy groups,
$E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —OCOE$_{11}$, —OE$_4$, —NCO, —NHCOE$_{11}$, or —NE$_7$E$_8$, or mixtures thereof, where $E_4$ is straight or branched chain alkyl of 1 to 24 carbon atoms; alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof; or $E_2$ is —(CH$_2$)$_m$—CO—E$_5$;
$E_5$ is OE or NE$_7$E$_8$, or
$E_5$ is —PO(OE$_{12}$)$_2$, —OSi(E$_{11}$)$_3$ or —OCO—E$_{11}$, or straight or branched chain C$_1$–C$_{24}$alkyl which can be interrupted by —O—, —S— or —NE$_{11}$ and which can be unsubstituted or substituted by —OH or —OCO—E$_{11}$, C$_5$–C$_{12}$cycloalkyl which is unsubstituted or substituted by —OH, straight chain or branched C$_2$–C$_{18}$alkenyl which is unsubstituted or substituted by —OH, C$_7$–C$_{15}$aralkyl, —CH$_2$—CHOH—E$_{13}$ or glycidyl,
$E_6$ is hydrogen, straight or branched chain C$_1$–C$_{24}$alkyl which is unsubstituted or substituted by one or more OH, OE$_4$ or NH$_2$ groups, or —OE$_6$ is —(OCH$_2$CH$_2$)$_w$OH or —(OCH$_2$CH$_2$)$_w$OE$_{21}$ where w is 1 to 12 and E$_{21}$ is alkyl of 1 to 12 carbon atoms,
$E_7$ and $E_8$ are independently hydrogen, alkyl of 1 to 18 carbon atoms, straight or branched chain alkenyl of 2 to 18 carbon atoms, straight or branched chain C$_3$–C$_{18}$alkyl which is interrupted by —O—, —S— or —NE$_{11}$—, C$_5$–C$_{12}$cycloalkyl, C$_6$–C$_{14}$aryl or C$_1$–C$_3$hydroxylalkyl, or E$_7$ and E$_8$ together with the N atom are a pyrrolidine, piperidine, piperazine or morpholine ring, or
$E_5$ is —X—(Z)$_p$—Y—E$_{15}$
wherein
X is —O— or —N(E$_{16}$)—,
Y is —O— or —N(E$_{17}$)—,
Z is C$_2$–C$_{12}$-alkylene, C$_4$–C$_{12}$-alkylene interrupted by one to three nitrogen atoms, oxygen atoms or a mixture thereof, or is C$_3$–C$_{12}$-alkylene, butenylene, butynylene, cyclohexylene or phenylene, each substituted by a hydroxyl group,
m is zero, 1 or 2,
p is 1, or p is also zero when X and Y are —N(E$_{16}$)— and —N(E$_{17}$)—, respectively,
$E_{15}$ is a group —CO—C(E$_{18}$)=C(H)E$_{19}$ or, when Y is —N(E$_{17}$)—, forms together with E$_{17}$ a group —CO—CH=CH—CO—, wherein E$_{18}$ is hydrogen or methyl, and E$_{19}$ is hydrogen, methyl or —CO—X—$E_{20}$, wherein $E_{20}$ is hydrogen, $C_1$–$C_{12}$-alkyl or a group of the formula

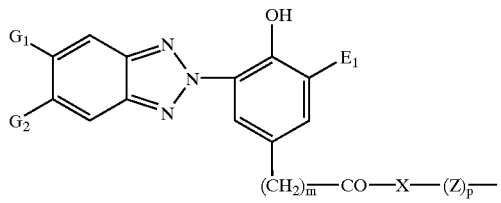

wherein the symbols $E_1$, $G_2$, X, Z, m and p have the meanings defined above, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene, $E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, and $E_{13}$ is H, straight chain or branched $C_1$–$C_{18}$alkyl which is substituted by —PO(O$E_{12}$)$_2$, phenyl which is unsubstituted or substituted by OH, $C_7$–$C_{15}$aralkyl or —CH$_2$O$E_{12}$, with the proviso that when concentrated sulfuric acid and alkali metal nitrite are used, $E_1$ and $E_2$ are alkyl of 1 to 4 carbon atoms; or $E_1$ can also be hydrogen.

In the above-described process, it is contemplated that the group $G_2$ may also be phenyl, naphthyl, biphenylyl or 9-phenanthryl substituted by electron-withdrawing groups as described in co-pending application Ser. No. 09/722,876, filed Nov. 27, 2000. For example, $G_2$ may be phenyl further substituted by perfluoroalkyl of 1 to 12 carbon atoms. The disclosure of application Ser. No. 09/722,876 is hereby incorporated by reference.

For example, the instant process involves the preparation of a compound of formula (Ia)

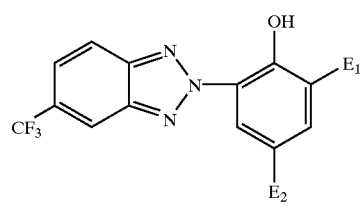

which process comprises
diazotizing a substituted o-nitroaniline compound of formula (IIa)

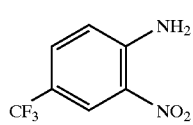

using concentrated sulfuric acid and sodium nitrite or nitrosylsulfuric acid to form the diazonium salt of formula (IIIa)

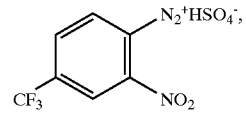

coupling said diazonium salt with a phenol of formula (IVa)

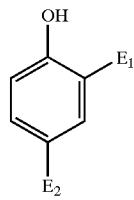

to form the corresponding monoazobenzene compound of formula (Va)

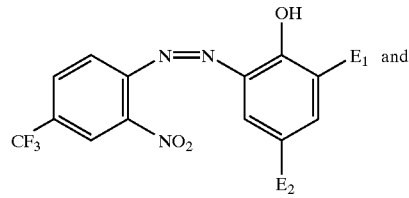

reducing the monoazobenzene intermediate of formula (Va) to the corresponding 2H-benzotriazole compound of formula (Ia) by conventional reduction means;

with the proviso that when concentrated sulfuric acid and alkali metal nitrite are used, $E_1$ and $E_2$ are alkyl of 1 to 4 carbon atoms; or $E_1$ can also be hydrogen.

For example, in the compound of formula (I),
$G_1$ is hydrogen,
$G_2$ is —CF$_3$,
$E_1$, is phenylalkyl of 7 to 15 carbon atoms, phenyl, or said phenyl or said phenylalkyl substituted on the phenyl ring by one to three alkyl of 1 to 4 carbon atoms,
$E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —OCO$E_{11}$, —O$E_4$, —NCO, —NH$_2$, —NHCO$E_{11}$, —NH$E_4$ or —N($E_4$)$_2$, or mixtures thereof, where $E_4$ is straight or branched chain alkyl of 1 to 24 carbon atoms; or said alkyl or said alkenyl interrupted by one or more —O—, —NH— or —N$E_4$— groups or mixtures thereof and which can be unsubstituted or substituted by one or more —OH, —O$E_4$ or —NH$_2$ groups or mixtures thereof; or
is a compound of formula (I) wherein,
$G_1$ is hydrogen,
$G_2$ is —CF$_3$,
$E_1$ is hydrogen or straight or branched alkyl of 4 to 24 carbon atoms, and $E_2$ is as defined above.

For example, the compound of formula (I) is also where
$G_1$ is hydrogen,
$G_2$ is —$CF_3$,
$E_1$ is hydrogen, straight or branched alkyl of 4 to 24 carbon atoms or phenylalkyl of 7 to 15 carbon atoms,
$E_2$ is $(CH_2)_m$—CO—$E_5$,
$E_5$ is —$OE_6$ or —$NE_7E_8$, or
$E_5$ is —X—$(Z)_p$—Y—$E_{15}$
wherein
X is —O— or —$N(E_{16})$—,
Y is —O— or —$N(E_{17})$—,
Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group,
m is 0, 1, 2 or 3,
p is 1, or p is also zero when X and Y are —$N(E_{16})$— and —$N(E_{17})$—, respectively,
$E_{15}$ is a group —CO—$C(E_{18})$=$C(H)E_{19}$ or, when Y is —$N(E_{17})$—, forms together with $E_{17}$ a group —CO—CH=CH—CO—, wherein $E_{18}$ is hydrogen or methyl, and $E_{19}$ is hydrogen, methyl or —CO—X—$E_{20}$, wherein $E_{20}$ is hydrogen, $C_1$–$C_{12}$-alkyl or a group of the formula

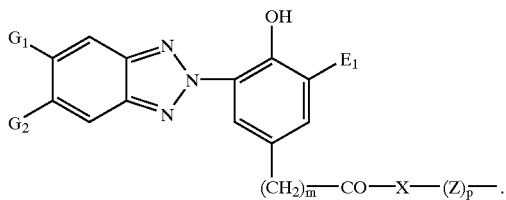

For instance, the compound of formula (I) is where
$G_1$ is hydrogen,
$G_2$ is —$CF_3$,
$E_1$, is phenylalkyl of 7 to 15 carbon atoms, phenyl, or said phenyl or said phenylalkyl substituted on the phenyl ring by one to three alkyl of 1 to 4 carbon atoms,
$E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —$OCOE_{11}$, —$NH_2$ or —$NHCOE_{11}$, or mixtures thereof, or said alkyl or said alkenyl interrupted by one or more —O— and which can be unsubstituted or substituted by one or more —OH; or
is a compound of formula (I) wherein,
$G_1$ is hydrogen,
$G_2$ is —$CF_3$,
$E_1$ is hydrogen, straight or branched alkyl of 4 to 24 carbon atoms or phenylalkyl of 7 to 15 carbon atoms, and
$E_2$ is as defined above.
For instance, the compound of formula (I) is where
$G_1$ is hydrogen,
$G_2$ is —$CF_3$,
$E_1$, is hydrogen, straight or branched alkyl of 4 to 24 carbon atoms or phenylalkyl of 7 to 15 carbon atoms, $E_2$ is —$(CH_2)_m$—CO—$E_5$,
$E_5$ is —$OE_6$ or —$NE_7E_8$ where
$E_6$ is hydrogen, straight or branched chain $C_1$–$C_{24}$alkyl which is unsubstituted or substituted by one or more OH groups, or —$OE_6$ is —$(OCH_2CH_2)_w$OH or —$(OCH_2CH_2)_wOE_{21}$ where w is 1 to 12 and $E_{21}$ is alkyl of 1 to 12 carbon atoms, and
$E_7$ and $E_8$ are independently hydrogen, alkyl of 1 to 18 carbon atoms, straight or branched chain $C_3$–$C_{18}$alkyl which is interrupted by —O—, —S— or —$NE_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring.

Illustrative of the compounds of formula (I) which can be made by the instant process are
(a) 5-trifluoromethyl-2-(2-hydroxy-3-α-cumyl-5-tert-octylphenyl)-2H-benzotriazole;
(b) 5-trifluoromethyl-2-(2-hydroxy-5-tert-octylphenyl)-2H-benzotriazole;
(c) 5-trifluoromethyl-2-(2-hydroxy-3,5-di-tert-octylphenyl)-2H-benzotriazole;
(d) 5-trifluoromethyl-2-[2-hydroxy-5-(2-hydroxyethyl)phenyl]-2H-benzotriazole;
(e) 5-trifluoromethyl-2-(2-hydroxy-3,5-di-α-cumylphenyl)-2H-benzotriazole;
(f) 3-(5-trifluoromethyl-2H-benzotriazol-2-yl)-5-tert-butyl-4-hydroxyhydrocinnamic acid;
(g) methyl 3-(5-trifluoromethyl-2H-benzotriazol-2-yl)-5-tert-butyl-4-hydroxyhydrocinnamate;
(h) isooctyl 3-(5-trifluoromethyl-2H-benzotriazol-2-yl)-5-tert-butyl-4-hydroxyhydrocinnamate;
(i) 5-trifluoromethyl-2-[2-hydroxy-5-(3-hydroxypropyl)phenyl]-2H-benzotriazole;
(j) 5-trifluoromethyl-2-[2-hydroxy-5-(3-acryloyloxypropyl)phenyl]-2H-benzotriazole;
(k) 5-trifluoromethyl-2-[2-hydroxy-5-(3-methacryloyloxypropyl)phenyl]-2H-benzotriazole;
(l) 5-trifluoromethyl-2-[2-hydroxy-5-(3-acrylylaminopropyl)phenyl]-2H-benzotriazole;
(m) 5-trifluoromethyl-2-[2-hydroxy-5-(3-methacrylylaminopropyl)phenyl]-2H-benzotriazole;
(n) 5-trifluoromethyl-2-(2-hydroxy-3-α-cumyl-5-tert-butylphenyl)-2H-benzotriazole;
(o) 5-trifluoromethyl-2-(2-hydroxy-3-α-cumyl-5-nonylphenyl)-2H-benzotriazole;
(p) 5-trifluoromethyl-2-[2-hydroxy-3-α-cumyl-5-(2-hydroxyethyl)phenyl]-2H-benzotriazole;
(q) 5-trifluoromethyl-2-[2-hydroxy-3-α-cumyl-5-(3-hydroxypropyl)phenyl]-2H-benzotriazole;
(r) 5-trifluoromethyl-2-(2-hydroxy-3,5-ditert-amylphenyl)-2H-benzotriazole;
(s) 5-trifluoromethyl-2-(2-hydroxy-3,5-ditert-butylphenyl)-2H-benzotriazole;
(t) 5-trifluoromethyl-2-(2-hydroxy-3-dodecyl-5-methylphenyl)-2H-benzotriazole;
(u) 5-trifluoromethyl-2-[2-hydroxy-3-tert-butyl-5-(3-hydroxypropyl)phenyl]-2H-benzotriazole; and
(v) 5-trifluoromethyl-2-[2-hydroxy-3-tert-butyl-5-(2-hydroxyethyl)phenyl]-2H-benzotriazole;

For example, the instant process involves the preparation of a compound of formula (Ib),

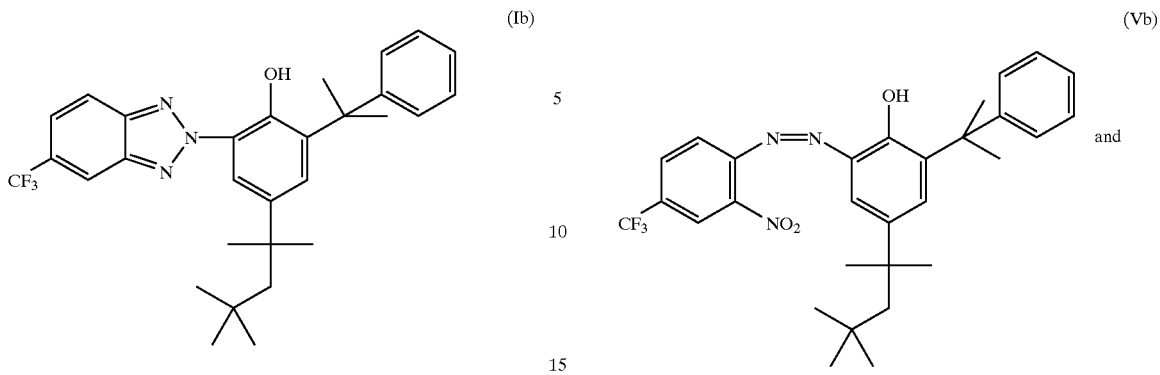

which process comprises diazotizing a substituted o-nitroaniline compound of formula (IIa)

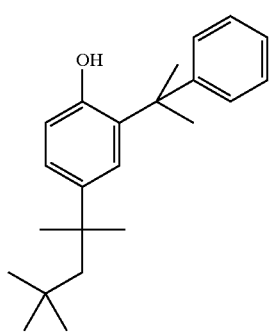

using nitrosylsulfuric acid to form the diazonium salt of formula (IIIa)

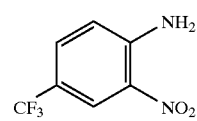

coupling said diazonium salt with a phenol of formula (IVb)

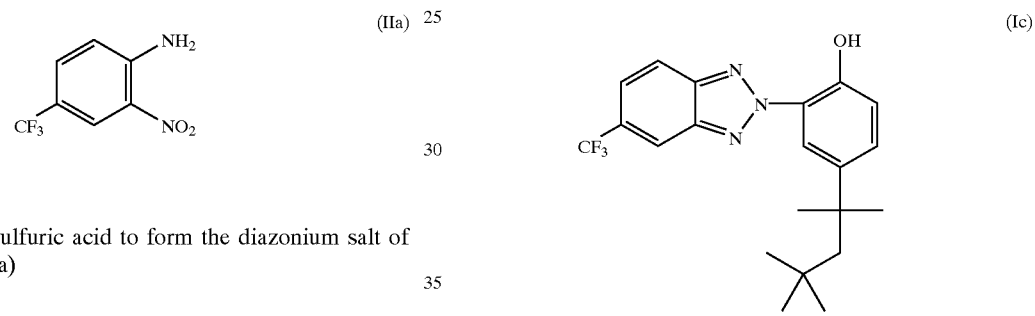

to form the corresponding monoazobenzene compound of formula (Vb)

reducing the monoazobenzene intermediate of formula (Vb) to the corresponding 2H-benzotriazole compound of formula (Ib) by conventional reduction means.

For instance, the instant process involves the preparation of a compound of formula (Ic),

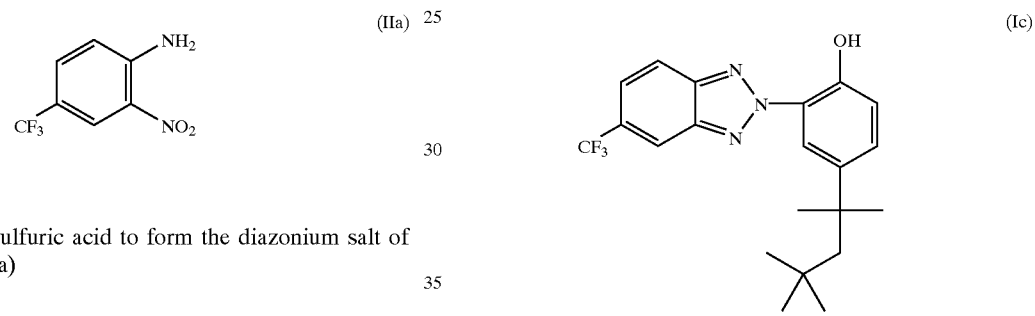

which process comprises diazotizing a substituted o-nitroaniline compound of formula (IIa)

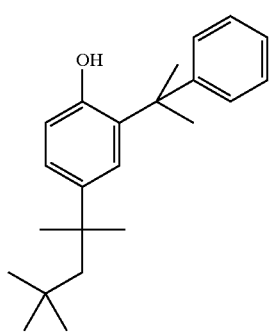

using nitrosylsulfuric acid to form the diazonium salt of formula (IIIa)

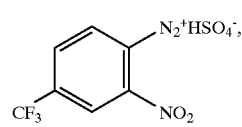

coupling said diazonium salt with a phenol of formula (IVc)

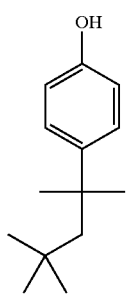

to form the corresponding monoazobenzene compound of formula (Vc)

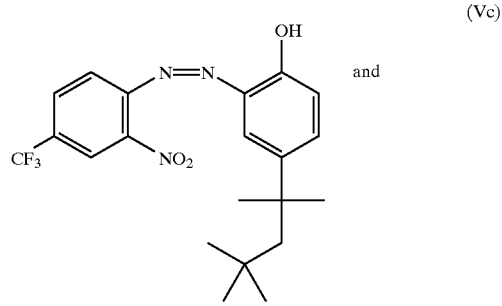

and reducing the monoazobenzene intermediate of formula (Vc) to the corresponding 2H-benzotriazole compound of formula (Ic) by conventional reduction means. Ia. In the process for making the diazonium salts using a perfluoroalkyl substituted o-nitroaniline (i.e. 4-trifluoromethyl-2-nitroaniline, $CF_3$-ONA), sulfuric acid and an aqueous alkali metal nitrite (i.e. sodium nitrite) solution, the following process parameters pertain:

a. The molar ratio of $CF_3$-ONA:sulfuric acid is 1:10 to 1:1; for example 1:5 to 1:1; for instance 1:2–3.5.

b. The molar ratio of $CF_3$-ONA:sodium nitrite is 1:1 to 1:4; for example 1:1 to 1:2; for instance 1:1.

c. The temperature used for this reaction is from −30° C. to 50° C.; for example from −20° C. to 20° C.; for instance from −10° C. to 5° C.

Ib. In the process for making the diazonium salts using a perfluoroalkyl substituted o-nitroaniline (i.e. 4-trifluoromethyl-2-nitroaniline, $CF_3$-ONA) and nitrosylsulfuric acid in sulfuric acid, the following process parameters pertain:

a. The molar ratio of $CF_3$-ONA:nitrosylsulfuric acid is 1:1 to 1:2; for example 1:1 to 1:1.2; for instance 1:1.

b. The molar ratio of $CF_3$-ONA:sulfuric acid is 1:1 to 1:10; for example 1:2 to 1:7; for instance 1:2 to 1:5.

c. The temperature used for this reaction is from −30° C. to 50° C.; for example from −20° C. to 40° C.; for instance from 0° C. to 25° C.

When preparing a diazonium salt using nitrosylsulfuric acid, a very low amount of water is required. The system is essentially anhydrous. When sulfuric acid concentrations are under 90%, nitrosylsulfuric acid becomes nitric oxide (NO) and evolves as a gas before it has time to react with the $CF_3$-ONA. At the end of the diazotization reaction, the diazonium salt solution in sulfuric acid is diluted with water to about 20–25%.

II. For the preparation of the monoazobenzene intermediate, there are two different coupling methods possible. The alkaline coupling method is described in detail in U.S. Pat. Nos. 4,275,004 and 4,347,180 which are incorporated herein by reference.

The acidic coupling process is described in detail in U.S. Pat. No. 5,436,322 which is incorporated herein by reference.

It is noted that instant Example 9 shows a coupling method which neither strongly alkaline nor strongly acidic. Rather, this Example shows coupling which is buffered with acetic acid and sodium hydroxide.

The details of the present specific acidic coupling method are described infra.

The diazonium salt formed as described above is reacted with the appropriate phenol in a solvent containing a surface active modifier at a temperature of −30° C. to 75° C.; for example at −20° C. to 50° C.; for instance at −10° C. to 35° C.

The solvents used are water, an aromatic hydrocarbon, an aliphatic hydrocarbon or a mixture thereof. For instance, the solvent is water, toluene, o-xylene, m-xylene, p-xylene or a mixture of said xylenes, mesitylene, pseudocumene, hexane, heptane, octane, nonane or a mixture thereof. For example, the solvent is water, toluene, o-xylene, m-xylene, p-xylene, a mixture of said xylenes, heptane or a mixture thereof.

The amount of solvent to be used is that sufficient to dissolve the reactants. The amount of solvent is not critical, but making the solution too dilute is to be avoided.

The surface active modifier to be used is any one or a mixture of materials selected from the group consisting of emulsifying agents, surfactants, phase transfer agents and dispersants.

For instance, the surface active modifier is HOSTAPUR® SAS93 (Hoechst) or PETROSUL® M-60 (Penreco). The amount used is that needed to ensure adequate mixing of the reactants.

The molar ratio of diazonium salt:phenol is 2:1 to 1:2; for example 1.5:1 to 1:1.5; for instance 1:1.

III. The monoazobenzene compounds prepared in the instant process can be conveniently reduced to the corresponding benzotriazolyl-1-oxide and then to the corresponding 2H-benzotriazole by any number of conventional reduction methods. An illustrative list of such methods is given below, but should not be construed as being the only methods possible for carrying out said reduction.

1. EP 0380840 A1 describes the hydrogenation of a benzotriazolyl-1-oxide to the benzotriazole using palladium/carbon catalyst in toluene/water and in the presence of dimethylamine.

2. EP 0380840 A1 also discloses the hydrogenation of a benzotriazolyl-1-oxide to the benzotriazole using Raney nickel catalyst in toluene/2-butanol and in the presence of 1,5-diazabicyclo[5.4.0]undecane.

3. EP 0380839 A1 discloses the hydrogenation of a nitromonoazobenzene to the benzotriazole using Raney nickel catalyst in toluene/isopropanol and in the presence of sodium hydroxide.

4. EP 0380839 A1 also discloses the hydrogenation of a nitromonoazobenzene to the benzotriazole using palladium/carbon catalyst in toluene/water/isopropanol and in the presence of dimethylamine.

5. Japanese Sho 37-5934 (1962) and U.S. Pat. No. 3,773,751 describe the reduction of a nitromonoazobenzene to the benzotriazole using zinc, sodium hydroxide in an alcohol.

6. U.S. Pat. No. 2,362,988 discloses a variety of methods for the reduction of a nitromonoazobenzene to a benzotriazole. These include the use of:

a. ammonium sulfide;
b. an alkali metal sulfide;
c. zinc and ammonia;
d. hydrogen sulfide and sodium; or
e. zinc and hydrochloric acid.

7. Japanese Sho 56-133076 (1981) describes the reduction of a nitromonoazobenzene to a benzotriazole using quinone plus a variety of coreactants. These include:
   a. zinc;
   b. ammonium sulfide;
   c. alkali metal sulfide;
   d. alkali metal hydrosulfide; or
   e. hydrazine.

8. Japanese Sho 52-113973 (1977) and Sho 52-113974 (1977) describe the hydrogenation of a nitromonoazobenzene to a benzotriazole using a precious metal catalyst in the presence of a base.

9. Japanese Sho 59-170172 (1984) and Sho 63-72682 (1988) describe the reduction of a nitromonoazobenzene to a benzotriazole using a quinone or an aromatic ketone in the presence of an alcohol and a base and with heating.

10. Japanese Sho 61-215378 (1986) describes the reduction of a nitromonoazobenzene or a benzotriazolyl-1-oxide benzotriazole to a benzotriazole using an aldehyde and aromatic ketone in the presence of a base.

11. Japanese Sho 63-72683 (1988) and U.S. Pat. No. 4,780,541 describe the reduction of a nitromonoazobenzene or a benzotriazolyl-1-oxide benzotriazole to a benzotriazole using a primary or secondary alcohol and an aromatic ketone in the presence of a base.

12. Japanese Sho 63-186886 (1988) describes the electrolytic reduction of a nitromonoazobenzene or a benzotriazolyl-1-oxide benzotriazole to a benzotriazole using an alkali metal hydroxide in water or an aqueous alcohol solution.

13. Japanese Sho 61-215379 (1986) and U.S. Pat. No. 4,789,541 describe the reduction of a benzotriazolyl-1-oxide benzotriazole to a benzotriazole using an aldehyde and an aromatic ketone in the presence of a base.

14. U.S. Pat. No. 5,571,924 describes the reduction of a nitromonoazobenzene or a benzotriazolyl-1-oxide benzotriazole to a benzotriazole using hydrazine and a precious metal catalyst.

15. U.S. Pat. No. 3,978,074 discloses the reduction of a nitromonoazobenzene to a benzotriazole using a hydrogen and a noble metal catalyst in the presence of an aqueous alkali metal hydroxide solution.

16. U.S. Pat. No. 4,219,480 discloses the reduction of a nitromonoazobenzene to a benzotriazole using a hydrogen and a Raney nickel catalyst in the presence of an aqueous alkali metal hydroxide solution or in the presence of an aliphatic amine.

17. U.S. Pat. No. 4,230,867 discloses the reduction of a nitromonoazobenzene to a benzotriazole using a hydrogen and a noble metal catalyst in the presence of an aliphatic amine.

One-pot Process for the Preparation of 2-(2-Nitrophenylazo) phenols

The present invention also provides a facile and improved multiphase process for the preparation of 2-(2-nitrophenylazo) substituted phenols and corresponding benzotriazole UV absorbers. The instant one-pot process is a highly efficient and environmentally acceptable ("Green Chemistry: Theory and Practice" by P. T. Anastas and J. C. Warner, Oxford press, 1998) in that: 1) The process can be carried out using environmentally friendly solvents (water, hydrocarbons, etc.); 2) The amount of corrosive, mineral acid required is low, decreasing waste handling issues and the formation of hazardous by-products; 3) It also offers safety advantages in that the diazonium salt is not isolated or processed in any way. The intermediate diazonium salt is generated in situ and reacted immediately, keeping diazonium concentrations to a minimum thereby minimizing the risk of explosion, worker exposure or release to the environment. For reagents containing fluorinated groups, the risk of generation and release of hazardous HF is eliminated; 4) The less stringent conditions produce fewer by-products resulting in higher yield and better product quality; 5) The process utilizes a single vessel eliminating the risk of transferring hazardous materials from one vessel to another; and 6) Cycle time is decreased resulting in better energy efficiency.

It is very surprising that the single vessel, simultaneous diazotization-coupling reaction works so well given that phenols are readily oxidized and nitrated under the same reaction conditions. See for example March, J, "Advanced Organic Chemistry," Fourth Ed., New York, pages 522–523.

Specifically, the instant one-pot process allows for the efficient preparation of a new class of benzotriazole ultraviolet light absorbers (UVA's), that is benzotriazole UVA's substituted in the 5 position of the benzo ring with a —$CF_3$ group. Further, surprisingly, the present process may be applied to the preparation of 2-(2-nitrophenylazo) substituted phenol (monoazo) intermediates of previously known commercial benzotriazole UVA's, that is benzotriazole UVA's with weaker electron withdrawing groups in the benzo ring (such as chloro) or benzotriazole UVA's with no electron withdrawing groups in the benzo ring. The environmental and safety benefits of the instant process are also realized in the preparation of these currently commercially available benzotriazoles.

Specifically, provided is a novel process for the preparation of 2-(2-nitrophenylazo) substituted phenols of the formula (VI)

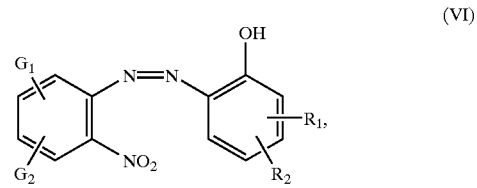

(VI)

which process comprises combining an ortho-nitroaniline of formula (VII)

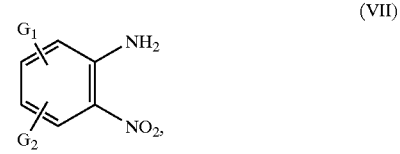

(VII)

a phenol of formula (VIII)

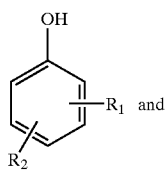

(VIII)

a nitrosating agent
together in a multiphase reaction medium and reacting the mixture for a sufficient time without isolation of intermediate products,
wherein the multiphase medium comprises an organic and an aqueous phase and optionally a surface active agent;
wherein
$G_1$ is hydrogen or chloro,
$G_2$ is perfluoroalkyl ($C_nF_{2n+1}$) where n is equal to 1–12, hydrogen, halogen, $NO_2$, cyano, $R_3S$—, $R_3SO$—, $R_3SO_2$—, phenyl, naphthyl, biphenylyl, 9-phenanthryl or said phenyl, naphthyl, biphenylyl or 9-phenanthryl substituted by one to three alkyl of 1 to 18 carbon atoms, phenylalkyl of 7 to 15 carbon atoms, $R_3S$—, $R_3SO$—, $R_3SO_2$, aryl of 6 to 10 carbon atoms, perfluoroalkyl of 1 to 12 carbon atoms, halogen, nitro, cyano, carboxyl, alkoxycarbonyl of 2 to 19 carbon atoms, hydroxyl, alkoxy of 1 to 18 carbon atoms, aryloxy of 6 to 10 carbon atoms, aralkoxy of 7 to 15 carbon atoms, vinyl, acetyl, acetamido, amino, dialkylamino of 2 to 12 carbon atoms, formyl, thioalkoxy of 1 to 18 carbon atoms, hydroxymethyl, aminomethyl, halomethyl, sulfato, phosphato or where any two substituents form a benzo ring with the aryl moiety to which they are attached,
$R_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $R_1$ is alkyl of 1 to 24 carbon atoms substituted by one or two hydroxy groups,
$R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $R_2$ is said alkyl of 1 to 24 carbon atoms or said alkenyl of 2 to 18 carbon atoms substituted by one or more —OH, —$OCOE_{11}$, —$OE_4$, —NCO, —$NHCOE_{11}$ or —$NE_7E_8$, or mixtures thereof, where $E_4$ is straight or branched chain alkyl of 1 to 24 carbon atoms; alkenyl of 2 to 18 carbon atoms; or said alkyl or said alkenyl interrupted by one or more —O—, —NH— or —$NE_4$— groups or mixtures thereof and which can be unsubstituted or substituted by one or more —OH, —$OE_4$ or —$NH_2$ groups or mixtures thereof; or $R_2$ is —$(CH_2)_m$—CO—$E_5$;
$R_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms;

$E_5$ is $OE_6$ or $NE_7E_8$, or $E_5$ is —$PO(OE_{12})_2$, —$OSi(E_{11})_3$ or —$OCO$—$E_{11}$, or straight chain $C_1$–$C_{24}$alkyl which can be interrupted by —O—, —S— or —$NE_{11}$ and which can be unsubstituted or substituted by —OH or —$OCO$—$E_{11}$, $C_5$–$C_{12}$cycloalkyl which is unsubstituted or substituted by —OH, straight chain or branched $C_2$–$C_{18}$alkenyl which is unsubstituted or substituted by —OH, $C_7$–$C_{15}$aralkyl, —$CH_2$–CHOH—$E_{13}$ or glycidyl,
$E_6$ is hydrogen, straight or branched chain $C_1$–$C_{24}$alkyl which is unsubstituted or substituted by one or more OH, $OE_4$ or $NH_2$ groups, or —$OE_6$ is —$(OCH_2CH_2)_w$OH or —$(OCH_2CH_2)_wOE_{21}$ where w is 1 to 12 and $E_{21}$ is alkyl of 1 to 12 carbon atoms,
$E_7$ and $E_8$ are independently hydrogen, alkyl of 1 to 18 carbon atoms, straight or branched chain alkenyl of 2 to 18 carbon atoms, straight or branched chain $C_3$–$C_{18}$alkyl which is interrupted by —O—, —S— or —$NE_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring, or
$E_5$ is —X—$(Z)_p$—Y—$E_{15}$
wherein
X is —O— or —$N(E_{16})$—,
Y is —O— or —$N(E_{17})$—,
Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group,
m is zero, 1 or 2,
p is 1, or p is also zero when X and Y are —$N(E_{16})$— and —$N(E_{17})$—, respectively,
$E_{15}$ is a group —CO—$C(E_{18})$=$C(H)E_{19}$ or, when Y is —$N(E_{17})$—, forms together with $E_{17}$ a group —CO—CH=CH—CO—, wherein $E_{18}$ is hydrogen or methyl, and $E_{19}$ is hydrogen, methyl or —CO—X—$E_{20}$, wherein $E_{20}$ is hydrogen, $C_1$–$C_{12}$-alkyl, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene,
$E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_{7-C15}$aralkyl,
$E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, and
$E_{13}$ is H, straight chain or branched $C_1$–$C_{18}$alkyl which is substituted by —$PO(OE_{12})_2$, phenyl which is unsubstituted or substituted by OH, $C_7$–$C_{15}$aralkyl or —$CH_2OE_{12}$.
Halogen is for example chloro, fluoro or bromo.
For instance, provided is a process for the preparation of a compound of formula (VIa)

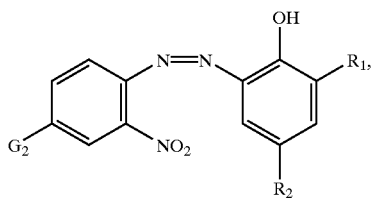

(VIa)

which process comprises combining an ortho-nitroaniline compound of formula (VIIa)

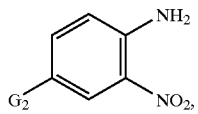

(VIIa)

a phenol of formula (VIIIa)

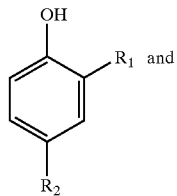

(VIIIa)

a nitrosating agent selected from concentrated sulfuric acid solution and sodium nitrite or nitrosylsulfuric acid, together in a two phase reaction medium comprising an organic and an aqueous phase and a surface active agent and reacting the mixture for a sufficient time without isolation of intermediate products.

A particular embodiment of the invention produces a compound of formula (VI) or (VIa) wherein $G_1$ is hydrogen, $G_2$ is —$CF_3$, halogen or hydrogen, $R_1$ is phenylalkyl of 7 to 15 carbon atoms, phenyl, or said phenyl or said phenylalkyl substituted on the phenyl ring by one to three alkyl of 1 to 4 carbon atoms, $R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —$OCOE_{11}$, —$OE_4$, —NCO, —$NH_2$, —$NHCOE_{11}$, —$NHE_4$ or —$N(E_4)_2$, or mixtures thereof, where $E_4$ is straight or branched chain alkyl of 1 to 24 carbon atoms; or said alkyl or said alkenyl interrupted by one or more —O—, —NH— or —$NE_4$— groups or mixtures thereof and which can be unsubstituted or substituted by one or more —OH, —$OE_4$ or —$NH_2$ groups or mixtures thereof; and $R_3$ is hydrogen; or a compound of formula (VI) or (VIa) wherein, $G_1$ is hydrogen, $G_2$ is —$CF_3$, halogen or hydrogen, $R_1$ is hydrogen or straight or branched alkyl of 4 to 24 carbon atoms, and $R_2$ and $R_3$ are as defined above.

In an alternative embodiment, the compound of formula (VI) or (VIa) is produced such that $G_1$ is hydrogen, $G_2$ is —$CF_3$ or halogen, $R_1$ is hydrogen, straight or branched alkyl of 4 to 24 carbon atoms or phenylalkyl of 7 to 15 carbon atoms, $R_2$ is $(CH_2)_m CO$—$E_5$, $R_3$ is hydrogen, $E_5$ is —$OE_6$ or —$NE_7E_8$, or $E_5$ is —X—$(Z)_p$—Y—$E_{15}$ wherein X is —O— or —$N(E_{16})$—, Y is —O— or —$N(E_{17})$—, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is 0, 1, 2 or 3, p is 1, or p is also zero when X and Y are —$N(E_{16})$— and —$N(E_{17})$—, respectively, $E_{15}$ is a group —CO—$C(E_{18})$=C(H)$E_{19}$ or, when Y is —$N(E_{17})$—, forms together with $E_{17}$ a group —CO—CH=CH—CO—, wherein $E_{18}$ is hydrogen or methyl, and $E_{19}$ is hydrogen, methyl or —CO—X—$E_{20}$, wherein $E_{20}$ is hydrogen, $C_1$–$C_{12}$-alkyl.

In a still further embodiment, the compound of formula (VI) or (VIa) is where $G_1$ is hydrogen, $G_2$ is —$CF_3$, $R_1$ is phenylalkyl of 7 to 15 carbon atoms, phenyl, or said phenyl or said phenylalkyl substituted on the phenyl ring by one to three alkyl of 1 to 4 carbon atoms, $R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —$OCOE_{11}$, —$NH_2$ or —$NHCOE_{11}$, or mixtures thereof, or said alkyl or said alkenyl interrupted by one or more —O— and which can be unsubstituted or substituted by one or more —OH; $R_3$ is hydrogen; or is a compound of formula (VI) or (VIa) wherein, $G_1$ is hydrogen, $G_2$ is —$CF_3$, $R_1$ is hydrogen, straight or branched alkyl of 4 to 24 carbon atoms or phenylalkyl of 7 to 15 carbon atoms, and $R_2$ and $R_3$ are as defined above.

A further embodiment is the compound of formula (VI) or (VIa) where $G_1$ is hydrogen, $G_2$ is —$CF_3$, $R_1$ is hydrogen, straight or branched alkyl of 4 to 24 carbon atoms or phenylalkyl of 7 to 15 carbon atoms, $R_2$ is —$(CH_2)_m$—CO—$E_5$, $R_3$ is hydrogen, $E_5$ is —$OE_6$ or —$NE_7E_8$ where $E_6$ is hydrogen, straight or branched chain $C_1$–$C_{24}$alkyl which is unsubstituted or substituted by one or more OH groups, or —OE$_6$ is —(OCH$_2$CH$_2$)$_w$OH or —(OCH$_2$CH$_2$)$_w$OE$_{21}$ where w is 1 to 12 and E$_{21}$ is alkyl of 1 to 12 carbon atoms, and E$_7$ and E$_8$ are independently hydrogen, alkyl of 1 to 18 carbon atoms, straight or branched chain C$_3$–C$_{18}$alkyl which is interrupted by —O—, —S— or —NE$_{11}$—, C$_5$–C$_{12}$cycloalkyl, C$_6$–C$_{14}$aryl or C$_1$–C$_3$hydroxylalkyl, or E$_7$ and E$_8$ together with the N atom are a pyrrolidine, piperidine, piperazine or morpholine ring.

Provided is a process for the preparation of a compound of formula (VIb)

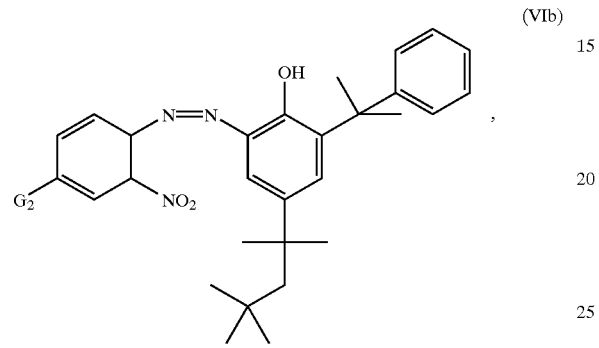

(VIb)

which process comprises combining an ortho-nitroaniline compound of formula (VIIb)

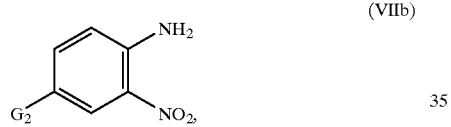

(VIIb)

a phenol of formula (VIIIb)

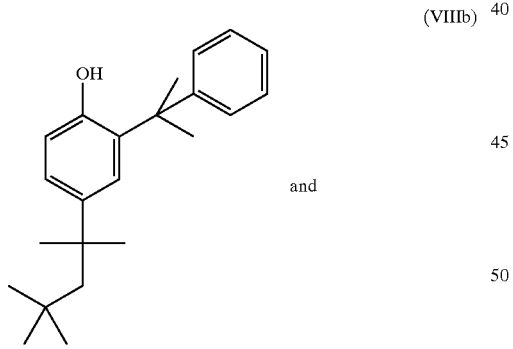

(VIIIb)

and nitrosylsulfuric acid in sulfuric acid together in a two phase reaction medium comprising an organic and an aqueous phase and a surface active agent and reacting the mixture for a sufficient time without isolation of intermediate products;

wherein G$_2$ is CF$_3$, hydrogen, fluorine, chlorine or bromine.

In this case the nitrosating agent, nitrosylsulfuric acid in sulfuric acid, may be added as an aqueous or an acid solution.

Provided is a process for the preparation of a compound of formula (VIc)

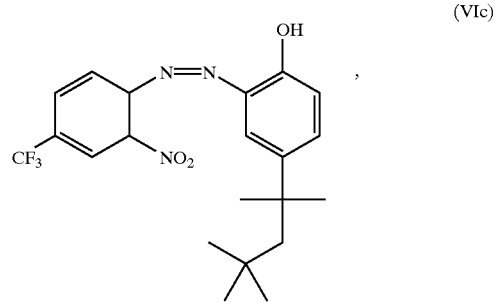

(VIc)

which process comprises combining an ortho-nitroaniline compound of formula (VIIc)

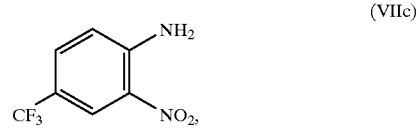

(VIIc)

a phenol of formula (VIIIc)

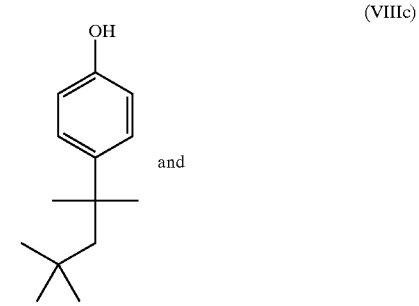

(VIIIc)

and nitrosylsulfuric acid in the form of an acid solution, together in a two phase reaction medium comprising an organic and an aqueous phase and a surface active agent and reacting the mixture for a sufficient time without isolation of intermediate products.

As discussed supra, intermediate products in the present process for the preparation of compounds of formula (VI) are not isolated. Specifically, diazonium salt products of the ortho-nitroaniline are not isolated.

In the present process where the nitrosating agent is sulfuric acid and alkali metal nitrite (i.e. sodium nitrite), the following process parameters pertain:

a. The molar ratio of nitroaniline: sulfuric acid is 1:10 to 1:1; for example 1:5 to 1:1; and for instance 1:3.5.

b. The molar ratio of nitroaniline: sodium nitrite is 1:1 to 1:4; for example 1:1 to 1:2; for instance 1:1.

c. The temperature used for this reaction is from –30° C. to 50° C.; for example from –20° C. to 20° C.; for instance from –10° C. to 5° C.

Ib. In the process for the in situ generation of diazonium salts using a substituted ortho-nitroaniline and nitrosylsulfuric acid in sulfuric acid, the following process parameters pertain:

a. The molar ratio of nitroaniline: nitrosylsulfuric acid is 1:1 to 1:2; for example 1:1 to 1:1.2; for instance 1:1.

b. The molar ratio of nitroaniline: sulfuric acid is 1:1 to 1:10; for example 1:2 to 1:7; for instance 1:2 to 1:5.

c. The temperature used for this reaction is from –30° C. to 50° C.; for example from –20° C. to 40° C.; for instance from 0° C. to 25° C.

When the nitrosating agent is nitrosylsulfuric acid and sulfuric acid, the concentration of the solution is under 90% since nitrosylsulfuric acid can decompose to form nitric oxide ($NO_x$) gases before it has time to react with the nitroaniline. A precharge of sulfuric acid may be used to limit the decomposition of nitrosulfuric acid and hence facilitate the diazotization reaction.

The present mixture is conveniently reacted at a temperature of −30° C. to 75° C.; for example at −20° C. to 50° C.; for instance at −10° C. to 35° C.

The organic solvents for use in the present multiphase process are selected from aromatic hydrocarbons, aliphatic hydrocarbons or mixtures thereof. Different solvents may be used for the dispersion and addition of phenolic compounds. For example, the organic solvent is ligroine, toluene, o-xylene, m-xylene, p-xylene or a mixture of said xylenes, mesitylene, pseudocumene, hexane, heptane, octane, nonane or a mixture thereof. For instance, the solvent is ligroine, toluene, o-xylene, m-xylene, p-xylene, a mixture of said xylenes, heptane or a mixture thereof. The amount of solvent is not critical, but making the solution too dilute is to be avoided. The essential attribute of the organic solvent is the ability to preferentially dissolve the phenolic compounds. The solvent must also be water immiscible as shown by phase separation when stirring is stopped.

The nitrosating agents are nitrosylsulfuric acid in an acid carrier or an aqueous alkali metal nitrite, such as sodium nitrite in an acidic environment. The nitrosating agent is for example a mixture of nitrosylsulfuric acid in sulfuric acid. Other appropriate acid carriers or acids include, without limitation, acetic acid, hydrochloric acid, fluoroboric acid. The ratio of organic solvent to water is for example 2:1 to 1:2. The acid is present in the reaction system prior to the addition of the nitrosating agent or added simultaneously therewith. The simultaneous addition can be done by separate addition or as a mixture (acid carrier). An acid carrier or acid environment is preferably present when preparing 2-(2-nitrophenylazo) substituted phenols from reagents characterized as electron deficient amines. Particular examples of electron deficient amines are trifluoromethyl, halogen and nitro-substituted aromatic amines, most especially when substituted by such groups in the 4-position of the benzene ring. Organic soluble buffers or bases increase the reactivity of the phenol toward the coupling reaction and limit the de-alkylation of the phenolic compound.

The surface active agent to be used is any one or a mixture of materials selected from the group consisting of emulsifying agents, surfactants, phase transfer agents and dispersants. For instance, the surface active modifier is at least one anionic surfactant. Suitable anionic surfactants include, for example, alcohol sulfates (e.g. alkali metal or ammonium salts of alcohol sulfates) and sulfonates, alcohol phosphates and phosphonates, alkyl sulfonates, alkylaryl sulfonates, alkali metal or ammonium salts of fatty acids, sulfonated amines, sulfonated amides, fatty sarcosinates such as sodium lauroyl sarcosinate, linear alkylated sulfonates such as alkylbenzene sulfonates where the R-group is attached between $C_6$–$C_{15}$, alcohol ether sulfates such as those with the structure R=$C_8$–$C_{15}$ and where ethoxylation is between 1–7, secondary alkane sulfonates such as the Hostapur® SAS series supplied by Clariant, and mixtures thereof. A more complete list of anionic surfactants is provided in McCutcheon's, Volume 1, Emulsifiers and Detergents, pp. 280–283 (1997), which is incorporated herein by reference. HOSTAPUR® SAS93 (Hoechst), which is a secondary alkane sulphonate sodium salt (paraffin sulphonate) or PETROSULS® M-60 (Penreco), which are petroleum sulphonate salts, are specific examples. The amount used is that needed to ensure adequate dispersion of the nitroaniline within the organic phase of the reaction system.

The molar ratio of nitroaniline:phenol may be for example 2:1 to 1:2; for example 1.5:1 to 1:1.5; for instance 1:1 to 1:0.85.

The 2-(2-nitrophenylazo) substituted phenol compounds of formula (VI) (monoazobenzene compounds) prepared by the instant process may be conveniently reduced to the corresponding benzotriazolyl-1-oxide and then to the corresponding 2H-benzotriazole by any number of conventional reduction methods. An illustrative list of such methods is given supra (references 1–17), and again should not be construed as being the only methods possible for carrying out said reduction.

Illustrative of the corresponding benzotriazole compounds that can be made from the 2-(2-nitrophenylazo) substituted phenols prepared by the present process are:

(1) 5-trifluoromethyl-2-(2-hydroxy-3-α-cumyl-5-tert-octylphenyl)-2H-benzotriazole;
(2) 5-trifluoromethyl-2-(2-hydroxy-5-tert-octylphenyl)-2H-benzotriazole;
(3) 5-trifluoromethyl-2-(2-hydroxy-3,5-di-tert-octylphenyl)-2H-benzotriazole;
(4) 5-trifluoromethyl-2-(2-hydroxy-5-(2-hydroxyethyl)phenyl)-2H-benzotriazole;
(5) 5-trifluoromethyl-2-(2-hydroxy-3,5-di-α-cumylphenyl)-2H-benzotriazole;
(6) 3-(5-trifluoromethyl-2H-benzotriazol-2-yl)-5-tert-butyl-4-hydroxyhydrocinnamic acid;
(7) methyl 3-(5-trifluoromethyl-2H-benzotriazol-2-yl)-5-tert-butyl-4-hydroxyhydrocinnamate;
(8) isooctyl 3-(5-trifluoromethyl-2H-benzotriazol-2-yl)-5-tert-butyl-4-hydroxyhydrocinnamate;
(9) 5-trifluoromethyl-2-[2-hydroxy-5-(3-hydroxypropyl)phenyl]-2H-benzotriazole;
(10) 5-trifluoromethyl-2-[2-hydroxy-5-(3-acryloyloxypropyl)phenyl]-2H-benzotriazole;
(11) 5-trifluoromethyl-2-[2-hydroxy-5-(3-methacryloyloxypropyl)phenyl]-2H-benzotriazole;
(12) 5-trifluoromethyl-2-[2-hydroxy-5-(3-acrylylaminopropyl)phenyl]-2H-benzotriazole;
(13) 5-trifluoromethyl-2-[2-hydroxy-5-(3-methacrylylaminopropyl)phenyl]-2H-benzotriazole;
(14) 5-trifluoromethyl-2-(2-hydroxy-3-α-cumyl-5-tert-butylphenyl)-2H-benzotriazole;
(15) 5-trifluoromethyl-2-(2-hydroxy-3-α-cumyl-5-nonylphenyl)-2H-benzotriazole;
(16) 5-trifluoromethyl-2-[2-hydroxy-3-α-cumyl-5-(2-hydroxyethyl)phenyl]-2H-benzotriazole;
(17) 5-trifluoromethyl-2-[2-hydroxy-3-α-cumyl-5-(3-hydroxypropyl)phenyl]-2H-benzotriazole;
(18) 5-trifluoromethyl-2-(2-hydroxy-3,5-di-tert-amylphenyl)-2H-benzotriazole;
(19) 5-trifluoromethyl-2-(2-hydroxy-3,5-di-tert-butylphenyl)-2H-benzotriazole;
(20) 5-trifluoromethyl-2-(2-hydroxy-3-dodecyl-5-methylphenyl)-2H-benzotriazole;
(21) 5-trifluoromethyl-2-[2-hydroxy-3-tert-butyl-5-(3-hydroxypropyl)phenyl]-2H-benzotriazole;
(22) 5-trifluoromethyl-2-[2-hydroxy-3-tert-butyl-5-(2-hydroxyethyl)phenyl]-2H-benzotriazole;
(23) 5-fluoro-2-(2-hydroxy-5-methylphenyl)-2H-benzotriazole;
(24) 5-chloro-2-(2-hydroxy-5-methylphenyl)-2H-benzotriazole;
(25) 5-bromo-2-(2-hydroxy-5-methylphenyl)-2H-benzotriazole;

(26) 5-chloro-2-(2-hydroxy-5-tert-octylphenyl)-2H-benzotriazole;
(27) 5-bromo-2-(2-hydroxy-5-tert-octylphenyl)-2H-benzotriazole;
(28) 5-chloro-2-(2-hydroxy-3,5-di-tert-butylphenyl)-2H-benzotriazole;
(29) 2-(2-hydroxy-5-methylphenyl)-2H-benzotriazole;
(30) 5-fluoro-2-(2-hydroxy-3,5-di-tert-butylphenyl)-2H-benzotriazole;
(31) 5-bromo-2-(2-hydroxy-3,5-di-tert-butylphenyl)-2H-benzotriazole;
(32) 2-(2-hydroxy-3,5-di-tert-butylphenyl)-2H-benzotriazole;
(33) 5-chloro-2-(2-hydroxy-3,5-di-α-cumylphenyl)-2H-benzotriazole;
(34) 5-fluoro-2-(2-hydroxy-3,5-di-α-cumylphenyl)-2H-benzotriazole;
(35) 5-chloro-2-(2-hydroxy-3-α-cumyl-5-tert-octylphenyl)-2H-benzotriazole;
(36) 5-bromo-2-(2-hydroxy-3-α-cumyl-5-tert-octylphenyl)-2H-benzotriazole;
(37) 5-fluoro-2-(2-hydroxy-3-α-cumyl-5-tert-octylphenyl)-2H-benzotriazole;
(38) 2-(2-hydroxy-3-α-cumyl-5-tert-octylphenyl)-2H-benzotriazole;
(39) 5-chloro-2-(2-hydroxy-4-phenylphenyl)-2H-benzotriazole;
(40) 5-fluoro-2-(2-hydroxy-4-phenylphenyl)-2H-benzotriazole;
(41) 5-bromo-2-(2-hydroxy-4-phenylphenyl)-2H-benzotriazole;
(42) 2-(2-hydroxy-3,5-di-α-cumylphenyl)-2H-benzotriazole;
(43) 5-chloro-2-[2-hydroxy-3-tert-butyl-5-(3-hydroxypropyl)phenyl]-2H-benzotriazole;
(44) 5-fluoro-2-[2-hydroxy-3-tert-butyl-5-(3-hydroxypropyl)phenyl]-2H-benzotriazole;
(45) 5-bromo-2-[2-hydroxy-3-tert-butyl-5-(3-hydroxypropyl)phenyl]-2H-benzotriazole;
(46) 2-[2-hydroxy-3-tert-butyl-5-(3-hydroxypropyl)phenyl]-2H-benzotriazole;
(47) 3-(5-chloro-2H-benzotriazol-2-yl)-5-tert-butyl-4-hydroxyhydrocinnamic acid;
(48) 3-(5-bromo-2H-benzotriazol-2-yl)-5-tert-butyl-4-hydroxyhydrocinnamic acid;
(49) 3-(5-fluoro-2H-benzotriazol-2-yl)-5-tert-butyl-4-hydroxyhydrocinnamic acid;
(50) 3-(2H-benzotriazol-2-yl)-5-tert-butyl-4-hydroxyhydrocinnamic acid;
(51) 3-(5-chloro-2H-benzotriazol-2-yl)-5-α-cumyl-4-hydroxyhydrocinnamic acid;
(52) 3-(5-bromo-2H-benzotriazol-2-yl)-5-α-cumyl-4-hydroxyhydrocinnamic acid;
(53) 3-(5-fluoro-2H-benzotriazol-2-yl)-5-α-cumyl-4-hydroxyhydrocinnamic acid;
(54) methyl 3-(2H-benzotriazol-2-yl)-5-tert-butyl-4-hydroxyhydrocinnamate;
(55) methyl 3-(5-chloro-2H-benzotriazol-2-yl)-5-tert-butyl-4-hydroxyhydrocinnamate;
(56) methyl 3-(5-chloro-2H-benzotriazol-2-yl)-5-α-cumyl-4-hydroxyhydrocinnamate;
(57) 5-chloro-2-(2-hydroxy-3,5-di-tert-amylphenyl)-2H-benzotriazole;
(58) 5-fluoro-2-(2-hydroxy-3,5-di-tert-amylphenyl)-2H-benzotriazole;
(59) 5-bromo-2-(2-hydroxy-3,5-di-tert-amylphenyl)-2H-benzotriazole;
(60) 2-(2-hydroxy-3,5-di-tert-amylphenyl)-2H-benzotriazole;
(61) 5-phenylsulfonyl-2-(2-hydroxy-3,5-di-tert-butylphenyl)-2H-benzotriazole;
(62) 5-octylsulfonyl-2-(2-hydroxy-3,5-di-tert-butylphenyl)-2H-benzotriazole;
(63) 5-phenylsulfonyl-2-(2-hydroxy-3,5-di-α-cumylphenyl)-2H-benzotriazole;
(64) 5-phenylsulfonyl-2-(2-hydroxy-3,5-di-α-cumylphenyl)-2H-benzotriazole;
(65) 5-phenylsulfonyl-2-(2-hydroxy-3-α-cumyl-5-tert-octylphenyl)-2H-benzotriazole;
(66) 5-octylsulfonyl-2-(2-hydroxy-3-α-cumyl-5-tert-octylphenyl)-2H-benzotriazole;
(67) 5-butylsulfonyl-2-(2-hydroxy-3-α-cumyl-5-tert-octylphenyl)-2H-benzotriazole;
(68) 5-ethylsulfonyl-2-(2-hydroxy-3-α-cumyl-5-tert-octylphenyl)-2H-benzotriazole;
(69) 5-n-dodecylsulfonyl-2-(2-hydroxy-3,5-di-tert-butylphenyl)-2H-benzotriazole;
(70) 5,5'-sulfonyl-bis[2-(2-hydroxy-3-α-cumyl-5-tert-octylphenyl)-2H-benzotriazole];
(71) octyl 3-(5-phenylsulfonyl-2H-benzotriazol-2-yl)-5-tert-butyl-4-hydroxyhydrocinnamate;
(72) 3-(5-phenylsulfonyl-2H-benzotriazol-2-yl)-5-tert-butyl-4-hydroxyhydrocinnamide; or
(73) 5-phenylsulfonyl-2-[2-hydroxy-3-tert-butyl-5-(3-hydroxypropyl)phenyl]-2H-benzotriazole;
(74) 2-(2-hydroxy-3,5-di-tert-octylphenyl)-2H-benzotriazole;
(75) 2-(2-hydroxy-5-tert-octylphenyl)-2H-benzotriazole;
(76) isooctyl 3-(2H-benzotriazol-2-yl)-5-tert-butyl-4-hydroxyhydrocinnamate; and
(77) 2-(3-t-butyl-2-hydroxy-5-(2-(ω-hydroxy-octa-(ethyleneoxy)carbonyl-ethyl)-, phenyl)-2H-benzotriazole, Tinuvin® 1130.

The following examples are for illustrative purposes only and are not to be construed to limit the scope of the instant invention in any manner whatsoever.

Examples 1–14 pertain to the improved process for the preparation of 5-perfluoroalkyl (for example trifluoromethyl) substituted 2H-benzotriazoles.

There are four generic procedures outlined in the Examples illustrating various methods of making the diazonium salts which are used to produce the desired monoazobenzene compounds by coupling with the appropriate phenol.

EXAMPLE 1

2-Nitrobenzenediazonium Chloride

To a laboratory reactor equipped with the necessary auxiliary attachments is added 206.4 g (32% by weight, 1.81 mol) of hydrochloric acid. o-Nitroaniline (82.6 g, 0.60 mol. ONA, Aldrich Chemical Co.) is added slowly to the well-stirred solution. An exotherm temperature of 40–50° C. occurs. After dissolution of the ONA is complete, ice (104 g, 5.78 mol) is charged and cooling is applied. At a temperature of −15° C. to −10° C., sodium nitrite (37.5 g, 0.60 mol) is charged slowly over a one-hour period while maintaining the temperature at −15° C. to −10° C. The resulting solution is clarified through a bed of Solka Floc (ground cellulose). A light yellow aqueous diazonium chloride salt solution is obtained in a yield of 410 g and is stored at about −15° C. to −10° C. till later use.

EXAMPLE 2

5-Trifluoromethyl-2-nitrobenzenediazonium Chloride

Following a procedure similar to that of Example 1, o-nitroaniline (ONA) is replaced with 4-trifluoromethyl-2- nitroaniline (CF$_3$-ONA). When 41.2 9 of CF$_3$-ONA (Aldrich Chemical Co.) is used, the title compound is obtained in a yield of 205 g as an aqueous solution and is stored at −15° C. to −10° C. till later use.

EXAMPLE 3

5-Trifluoromethyl-2-nitrobenzenediazonium Bisulfate

To a laboratory reactor equipped with necessary ancillary equipment, 93% sulfuric acid (99.5 g, 0.94 mol) is charged. 4-Trifluoromethyl-2-nitroaniline (63.9 g, 0.30 mol, obtained from Aldrich Chemical Co.) is added slowly to the well-stirred reaction mass. The reaction mass is heated to 70–75° C. to ensure complete dissolution. At this temperature, water (200 g, 11.1 mol) is added slowly while maintaining the temperature at 70–75° C. The reaction mixture is cooled to 0–5° C. at which time sodium nitrite (54.3 g, 0.32 mol, as a 40% aqueous solution) is charged over a two-hour period. The temperature should be kept in this temperature range since an exotherm can occur if the temperature is not monitored carefully. The resulting yellow solution is clarified through a bed of Solka Floc (ground cellulose). The yellow aqueous diazonium salt solution (400 g) is obtained and stored at −15° C. to −10° C. till later use.

EXAMPLE 4

5-Trifluoromethyl-2-nitrobenzenediazonium Bisulfate

To a laboratory reactor equipped with the necessary ancillary equipment, nitrosylsulfuric acid (384.7 g, 1.20 mol, 40% solution in sulfuric acid, obtained from Aldrich Chemical Co. or synthesized before use) and concentrated 98% sulfuric acid (287.3 g, 2.73 mol) are charged.

To the above solution well-stirred and cooled to 10–15° C., 4-trifluoromethyl-2-nitroaniline (250.7 g, 1.20 mol, obtained from Aldrich Chemical Co.) is charged portionwise over one to two hours while maintaining the temperature at 0° C. Ice (700 g, 38.9 mol) is charged slowly and the excess nitrosylsulfuric acid is destroyed with sulfamic acid. The yellow solution formed is clarified through a sintered glass funnel. The reactor and funnel are rinsed with cold water (100 g, 5.6 mol) and combined with the diazonium salt solution. The title compound is prepared in a yield of 1777.9 g as a yellow, aqueous solution which is stored at −15° C. to −10° C. until later use.

Examples 5–12 show the preparation of selected monoazobenzene compounds which are intermediates for preparing the corresponding 2H-benzotriazole UV abosrbers.

EXAMPLE 5

2-Hydroxy-2'-nitro-4'-trifluoromethyl-5-tert-octylazobenzene

To a laboratory reactor equipped with the necessary auxiliary equipment, 4-tert-octylphenol (36.0 g, 0.17 mol, obtained from Aldrich Chemical Co.), xylenes (90 g, 0.84 mol) and HOSTAPUR® SAS93 (1.5 g, surfactant, Hoechst Corp.) are charged. The reaction mixture is cooled to 10° C. at which time the diazonium salt solution, prepared in Example 2, (303 g, 0.17 mol, as a 14.3% solution) is charged over a three-hour period. The aqueous layer is separated after heating the reaction mass to 45° C. The xylene phase is analyzed for the title compound; standardized HPLC analysis reveals a 23.7% yield of the title compound.

EXAMPLE 6

2-Hydroxy-2'-nitro-4'-trifluoromethyl-3,5-di-tert-butylazobenzene

To a laboratory reactor equipped with the necessary auxiliary equipment, 2,4-di-tert-butylphenol (47.1 g, 0.22 mol, obtained from Schenectady Chemical Co.), xylenes (80 g, 0.75 mol) and PETROSUL® M-60 (1.8 g, surfactant, Penreco) are charged. At ambient temperature (20–25° C.), the diazonium salt solution prepared in Example 3 (344 g, 0.24 mol) is charged over a 4.25 hour period while continuing agitation for another six hours. Xylenes (300 g, 2.83 mol) and sodium hydroxide (183 g, 1.14 mol as a 25% aqueous solution) are charged while heating to 75° C. The aqueous layer is removed and the organic layer is subjected to vacuum distillation to remove xylenes. The crimson red oil obtained is crystallized from 120 g of methanol at 0° C. The solids are filtered and washed with 300 g of cold methanol. After vacuum drying, the title compound is prepared in 86.8% yield (82.3 g) as a solid melting at 105° C. The structure is verified by $^1$Hnmr and mass spectrometry analyses.

EXAMPLE 7

2-Hydroxy-2'-nitro-4'-trifluoromethyl-4,5-dimethylazobenzene (Major) 2-Hydroxy-2'-nitro-4'-trifluoromethyl-5,6-dimethylazobenzene (Minor)

Following the procedure of Example 6, 3,4-dimethylphenol (27.8 g, 0.23 mol) is substituted for 2,4-di-tert-butylphenol. The title compounds are obtained as 67.4 g, 86.4% yield as a crimson solid and is a 83:17 mixture of the two indicated regioisomers as judged by $^1$Hnmr analysis.

EXAMPLE 8

2-Hydroxy-2'-nitro-5-methylazobenzene

To a laboratory reactor equipped with the necessary auxiliary equipment, water (698 g, 38.8 mol), sodium hydroxide (49.2 g, 0.61 mol as a 50% aqueous solution) and p-cresol (66.9 g, 0.62 mol) are charged. After cooling to 0° C., the diazonium salt solution prepared in Example 1 (444 g, 0.60 mol as a 25% aqueous solution) is added over 3.5 hours. During the latter two hours of addition a pH of 8.0–9.0 is maintained (47.6 g of 50% aqueous sodium hydroxide is required.). Xylenes (310 g, 2.92 mol) and water (150 g, 8.33 mol) are charged while heating the solution to 84–86° C. The aqueous layer is removed and the organic layer is washed once with 300 g of water. The xylene phase is dried by azeotropic distillation. The title compound is obtained as a crimson red xylene solution (370 g, 96.1% yield as a 40% by weight solution).

EXAMPLE 9

2-Hydroxy-2'-nitro-4'-trifluoromethyl-5-tert-octylazobenzene

To a laboratory reactor equipped with the necessary ancillary equipment, xylenes (188.4 g, 1.78 mol), methanol (5.4 g, 0.17 mol), water (120 g, 6.67 mol), acetic acid (60 g, 1.0 mol) and p-tert-octylphenol (56.9 g, 0.28 mol) are charged. After cooling to −5° C., the diazonium salt solution prepared in Example 4 (424.2 g, 0.27 mol as a 19.7% aqueous solution) and sodium hydroxide (473 g, 2,37 mol as a 20% aqueous solution) are charged simultaneously over three hours. A thirty gram water rinse is charged after completion of the diazonium salt solution addition. The reaction mass is allowed to warm to 5° C. over two hours with continued stirring. Xylenes (50 g, 0.47 mol) is added following by heating to 40° C. The water phase is split off and the desired product is isolated from the xylene phase. The title compound is prepared as a crimson solid (82.7 g, 73.8% yield) whose structure is consistent with $^1$Hnmr analysis.

EXAMPLE 10

2-Hydroxy-2'-nitro-4'-trifluoromethyl-3-α-cumyl-5-tert-octylazobenzene

To a laboratory reactor equipped with the necessary ancillary equipment, xylenes (411.7 g, 3.88 mol), 2-α-cumyl-4-tert-octylphenol (232.8 g, 0.69 mol) and HOSTAPUR® SAS 93 (9.7 g, surfactant, Hoechst Corp.) are charged. After cooling to 0–5° C., the diazonium salt solution prepared in Example 4 (1115.4 g, 0.68 mol) is added over a 3.75 hour period. While the diazonium salt solution is added, the reaction mass is homogenized with an Ultraturax homogenizer. After the diazonium salt solution addition is complete, agitation is continued for another two hours. The reaction mass is heated to 55° C. and the aqueous layer is split off. From the organic phase, the title compound is obtained as a crimson red solid (282.9 g, 76.4% yield) melting at 101–105° C.

Examples 6 and 7 show that the diazonium salts produced using sulfuric acid and sodium nitrite as seen in Example 3 are useful for coupling with phenols having lower alkyl substitution (such as 3,4-dimethylphenol in Example 7 or 2,4-di-tert-butylphenol in Example 6). Examples 11 and 12 show that diazonium salts as prepared in Example 3 are not useful for coupling with phenols having longer alkyl chains (such as 4-tert-octylphenol) even though 2,4-di-tert-butylphenol and 4-tert-octylphenol have the same total number of alkyl carbon atoms as substituents.

EXAMPLE 11

2-Hydroxy-2'-nitro-4'-trifluoromethyl-5-tert-octylazobenzene

To a laboratory reactor equipped with the necessary auxiliary equipment, xylenes (201.4 g, 1.90 mol), p-tert-octylphenol (82.6 g, 0.39 mol) and HOSTAPUR® SAS 93 (3.4 g, surfactant, Hoechst Corp.) are charged. After cooling to 10–12° C., the diazonium salt solution prepared in Example 3 (874.9 g, 0.39 mol as a 14.05% aqueous solution) is added over a three-hour period. The reaction mass is heated to 25° C. and the aqueous layer is removed. The title compound is obtained from the xylene phase as a crimson solid in a yield of 61.47 g (37% yield).

EXAMPLE 12

2-Hydroxy-2'-nitro-4'-trifluoromethyl-5-tert-octylazobenzene

To a laboratory reactor equipped with the necessary auxiliary equipment, xylenes (15.3 g, 0.14 mol), p-tert-octylphenol (32.5 g, 0.15 mol), methanol (237.6 g, 7.42 mol), water (7.0 g, 0.39 mol) and sodium hydroxide (63.6 g, 1.59 mol) are added. The temperature is reduced to −15° C. to −10° C. at which time the diazonium salt solution prepared in Example 3 (311.2 g, 0.195 mol as a 19.8% aqueous solution) is added over a four-hour period. Water (190 g, 10.6 mol) and xylenes (304.5 g, 2.87 mol) are added while heating to 65° C. The aqueous layer is removed. The title compound is isolated from the xylene phase as a crimson solid in a yield of 21.6 g (33.8% yield).

Examples 5, 9, 11 and 12 show the synthesis of the same monoazo compound, namely 2-hydroxy-2'-nitro-4'-trifluoromethyl-5-tert-octylazobenzene, from the diazonium salt prepared from 4-trifluoro-2-nitroaniline (CF$_3$-ONA) and coupled with 4-tert-octylphenol. The diazonium salt solutions are prepared by different preparative methods as shown in Examples 2, 3 and 4. The yields for preparing the monoazo compounds are tabulated in the Table below showing that when a trifluoromethyl moiety is present that major differences in yield occur depending on how the diazonium salt is prepared regardless of the coupling method.

| Diazonium Salt of Example | Method of Making Diazonium Salt | Monoazo Yield (%) |
|---|---|---|
| 5 | NaNO$_2$ + HCl | 23.7 |
| 11 | NaNO$_2$ + H$_2$SO$_4$ | 37* |
| 12 | NaNO$_2$ + H$_2$SO$_4$ | 33.8** |
| 9 | nitrosylsulfuric | 73.8 |
| 10*** | nitrosylsulfuric | 76.4 |

*Acid coupled
**Base coupled
***The monoazo compound is 2-hydroxy-2'-nitro-3-α-cumyl-4'-trifluoromethyl-5-tert-octyl-azobenzene.

It is clear that the use of nitrosylsulfuric acid in the preparation of the diazonium salt where a trifluoromethyl moiety is present leads to far superior yields of the key monoazobenzene intermediate needed to prepare the instant benzotriazole UV absorbers.

When the monoazo compound is 2-hydroxy-2'-nitro-4'-trifluoromethyl-3,5-di-tert-butyl-azobenzene as seen in Example 6, the method of making the monoazo compound using NaNO$_2$+H$_2$SO$_4$ leads to a yield of 86.8% in contrast to the yields of 37% and 33.8% when the monoazo compound is 2-hydroxy-2'-nitro-4'-trifluoromethyl-5-tert-octylazobenzene made using NaNO$_2$+H$_2$SO$_4$ as seen in Examples 11 and 12.

Examples 13 and 14 show that the monoazobenzene compounds of the instant invention can be reduced to the desired 2H-benzotriazole UV absorber in excellent yield using any of a number of conventional methods such as, for example, by catalytic hydrogenation using hydrogen in a basic medium or reduction using 2,3-dichloro-1,4-naphthoquinone.

EXAMPLE 13

5-Trifluoromethyl-2-(2-hydroxy-5-tert-octylphenyl)-2H-benzotriazole

To a laboratory autoclave equipped with the necessary auxiliary equipment, the monoazo compound prepared in Example 9 (112.4 g, 0.25 mol), xylenes (160 g, 1.51 mol), n-butylamine (110 g, 1.50 mol) and platinum/palladium on carbon catalyst (1.5 g, Johnson Matthey Co.) are added. At a temperature of 20–25° C., hydrogen is metered slowly into the autoclave at a pressure of 30 psig. At the end of the reaction, the final reaction temperature is adjusted to 55° C. The hydrogen is vented and the catalyst is removed by filtration. The n-butylamine is removed by distillation and the reaction mass is cooled to 60° C. at which time it is washed with 134.5 g of 78% sulfuric acid. After splitting off the acid phase, the organic phase is washed twice with 200 g of water at 65–75° C. The xylene phase is dried by azeotropic distillation and then treated with 5 g of acidic alumina. After removal of the alumina, the xylene is distilled and replaced with 200 g of methanol and seeded. The slurry is cooled to 0° C., filtered and washed with 200 g of methanol and dried overnight at 65° C. in a vacuum oven. The title compound is obtained as a white powder (71.8 g, 71.6% yield) with a melting point of 80–81° C.

EXAMPLE 14

5-Trifluoromethyl-2-(2-hydroxy-3-α-cumyl-5-tert-octylphenyl)-2H-benzotriazole

To a laboratory reactor equipped with the necessary auxiliary equipment, 2-butanol (700 g, 9.46 mol) and sodium hydroxide pellets (23.7 g, 0.59 mol) are charged and heated to reflux. A solution of the monoazo compound prepared in Example 10 (122.4 g, 0.22 mol), 2,3-dichloro-1,4-naphthoquinone (5.6 g, 0.025 mol from the Aldrich Chemical Co.), heptane (342 g, 3.41 mol) and methyl ethyl ketone (402.5 g, 5.6 mol) is added to the refluxing solution over a two-hour period while distilling off methyl ethyl ketone and heptane. After the reaction is complete, the temperature is reduced to 45–50° C. at which time the reaction mass is neutralized with 30% aqueous sulfuric acid. The temperature is reduced to 25° C. and the reaction mass is seeded. After cooling to 5° C., the slurry is filtered and washed with 232 g of hot water. The filter cake is allowed to cool to ambient temperature and is then washed with 200 g of cold methanol and dried in a vacuum oven. The title compound is prepared in a yield of 92.8 g, 79.1% yield and has a melting point of 119–121° C.

Examples 15–30 pertain to the present one-pot process for the preparation of 2-(2-nitrophenylazo)phenols.

EXAMPLE 15

2-(2-Nitro-4-trifluoromethyl-phenylazo)-6-(1-methyl-1-phenyl-ethyl)-4-(1,1,3,3-tetramethyl-butyl)-phenol To a 1 L lab flask are added 54.6 g (0.26 mol, 99.9%) of 4-trifluoromethyl-2-nitroaniline, PETROSUL H-60 (5.3 g dissolved in 121.4 g water), 2-cumyl-4-tert-octylphenol (80.9 g, 0.25 mol, 92.5%) and ligroine (241.7 g, bp 90–110° C.). Sulfuric acid (32.7g, 93%) is charged to the reactor with stirring. The reaction mass is cooled to 5° C. Nitrosylsulfuric acid (94.4 g, 0.30 mol, 40% in sulfuric acid) and water (84.5 g) are added via a peristaltic pump over 8 hours. The cooling bath is removed and the reaction mass is allowed to warm to room temperature overnight. The reaction mass is heated to 40° C. Stirring is stopped and the two phases separate. Removed the aqueous layer. The ligroine layer weighed 373.8 g and contained 25.73 weight % of desired product (96.2 g of monoazo corresponding to a yield of 77% based on phenol as determined by calibrated HPLC analysis). The product may be crystallized from hot methanol, resulting in a burgundy solid with a melting point of 101–105° C. as per co-pending application 09/632217 example 10. $^{1}$H-NMR (CDCl$_3$; 499.8494 MHz): δ 0.85 (s, 9H); δ 1.42 (s, 6H); δ 1.77 (s, 2H); δ 1.78 (s, 6H); δ 7.14–7.30 (multiplet, 5H); δ 7.50 (d, 1H); δ 7.90 (d, 1H); δ 8.15 (d, 1H); δ 8.37 (s, 1H).

COMPARATIVE EXAMPLE 15c 2-(2-Nitro-4-trifluoromethyl-phenylazo)-6-(1-methyl-1-phenyl-ethyl)-4-(1,1,3,3-tetramethyl-butyl)-phenol Published British patent 2,319,035 (example) 1 reports a yield of 42.1 g of a paste. As demonstrated above the desired product is a solid with a well defined melting point. The fact that the product is a paste indicates that the monoazo obtained in GB 2,319,035 is impure. The purity is not specified. The yield of the paste of unknown purity is 38.5% based on 4-trifluoromethyl-2-nitroaniline using the traditional base coupling route.

EXAMPLE 16

2-(2-Nitro-4-trifluoromethyl-phenylazo)-6-(1-methyl-1-phenyl-ethyl)-4-(1,1,3,3-tetramethyl-butyl)-phenol Following the procedure of Example 15, substituting heptane as the solvent and using half the amount of sulfuric acid, the desired monoazo is obtained in a 68.4% yield based on phenol as determined by calibrated HPLC analysis.

EXAMPLE 17

2-(2-Nitro-4-trifluoromethyl-phenylazo)-6-(1-methyl-1-phenyl-ethyl)-4-(1,1,3,3tetramethyl-butyl)-phenol Following the procedure of Example 16, substituting hexane as the solvent, the desired monoazo is obtained in a 73.1% yield based on phenol as determined by calibrated HPLC analysis.

EXAMPLE 18

2-(2-Nitro-4-trifluoromethyl-phenylazo)-6-(1-methyl-1-phenyl-ethyl)-4-(1,1,3,3-tetramethyl-butyl)-phenol Following the procedure of Example 16, substituting xylene as the solvent, the desired monoazo is obtained in a 65.7% yield based on phenol as determined by calibrated HPLC analysis.

EXAMPLE 19

2-(2-Nitro-4-trifluoromethyl-phenylazo)-6-(1-methyl-1-phenyl-ethyl)-4-(1,1,3,3-tetramethyl-butyl)-phenol Following the procedure of Example 15, except eliminating the sulfuric acid precharge, the desired monoazo is obtained in a 76.3% yield based on phenol as determined by calibrated HPLC analysis.

EXAMPLE 20

2-(2-Nitro-4-trifluoromethyl-phenylazo)-6-(1-methyl-1-phenyl-ethyl)-4-(1,1,3,3-tetramethyl-butyl)-phenol Following the procedure of Example number 19, substituting Hostapur® SAS for the Petrosul® H-60 surfactant, the desired monoazo is obtained in a 71.7% yield based on phenol as determined by calibrated HPLC analysis.

EXAMPLE 21

2-(2-Nitro-4-trifluoromethyl-phenylazo)-6-(1-methyl-1-phenyl-ethyl)-4-(1,1,3,3-tetramethyl-butyl)-phenol Following the procedure of Example 18, except using a phenol to nitroaniline ratio of 0.91 instead of 0.86, the desired monoazo is obtained in a 59.5% yield based on phenol as determined by calibrated HPLC analysis.

EXAMPLE 22

2-(2-Nitro-4-trifluoromethyl-phenylazo)-6-(1-methyl-1-phenyl-ethyl)-4-(1,1,3,3-tetramethyl-butyl)-phenol Following the procedure of Example 15, except using heptane as the solvent, Hostapur® SAS as the surface active agent and adding 3 wt % 2,6-lutidine, the desired monoazo is obtained in a 65% yield based on 4-trifluoromethyl-2-nitroaniline as determined by calibrated HPLC analysis.

EXAMPLE 23

2-(2-Nitro-4-bromo-phenylazo)-6-(1-methyl-1-phenyl-ethyl)-4-(1,1,3,3-tetramethyl-butyl)-phenol Following the general procedure of Example 15 with heptane as the solvent, the title compound is prepared as a crimson solid with a melting point of 117–120° C. $^1$H-NMR (CDCl$_3$; 499.8494 MHz): δ 0.83 (s, 9H); δ 1.44 (s, 6H); δ 1.78 (s, 2H); δ 1.79 (s, 6H); δ 7.13–7.28 (multiplet, 5H); δ 7.62 (d, 1H); δ 7.68 (d, 1H); δ 7.79 (d, 1H); δ 7.85 (d, 1H); δ 8.19 (d, 1H); δ 12.94 (s, 1H). Elmental analysis: Calculated for C29H34BrN3O3: C 63.04; H 6.20; N 7.61. Found: C 62.76; H 6.01; N 7.28.

* 4-Bromo-2-nitroaniline prepared as per Elder, J. W.; Paolillo, M. A. *J. Chem. Ed.* 1994, 71(6), A144.

EXAMPLE 24

2-(2-Nitro-4-chloro-phenylazo)-6-(1-methyl-1-phenyl-ethyl)-4-(1,1,3,3-tetramethyl-butyl)-phenol Following the general procedure of Example 22, the title compound is prepared. Crystallization from xylene/methanol resulted in burgundy cubic crystals with a melting point of 127–131° C.; elemental analysis: calculated for C29H34ClN3O3. C, 68.56; H, 6.75; N, 8.27; Cl, 6.98. Found: C, 68.67; H, 6.81; N, 8.28; Cl, 6.99.

EXAMPLE 25

2-(2,4-di-Nitro-phenylazo)-6-(1-methyl-1-phenyl-ethyl)-4-(1,1,3,3-tetramethyl-butyl)-phenol Following the general procedure of Example 22, the title compound is prepared. Crystallization from xylene/methanol resulted in a purple-red, very fine needle-like solid with a melting point of 121–125° C. M.S.: a molecular ion of 518 in the positive ion mode is observed with a fragmentation pattern consistent with the desired product. $^1$H-NMR (CDCl$_3$; 499.8494 MHz): δ 0.88 (s, 9H); δ 1.40 (s, 6H); δ 1.73 (s, 2H); δ 1.76 (s, 6H); δ 7.14–7.30 (multiplet, 5H); δ 7.21 (d, 1H); δ 7.51 (d, 1H); δ 8.31 (d, 1H); δ 8.47 (d, 1H); δ 9.06 (d, 1H). Elemental analysis: Calculated for C29H34N4O5: C, 67.16; H, 6.61; N, 10.80. Found C, 67.09; H, 6.57; N, 10.83.

EXAMPLE 26

2-(2-Nitro-4-bromo-phenylazo)-4,6-di-tert-butyl Phenol

Following the general procedure of instant Example 22, the title compound is prepared. Crystallization from xylene/methanol resulted in burgundy needle shaped crystals with a melting point of 188–190° C. M.S. a molecular ion of 433 in the positive ion mode with a fragmentation pattern consistent with the desired structure is observed. $^1$H-NMR (CDCl$_3$; 499.8494 MHz): δ 1.37 (s, 9H); δ 1.46 (s, 9H); δ 7.51 (d, 1H); δ 7.65 (d, 1H); δ 7.84 (d, 1H); δ 8.25 (d, 1H); δ 13.60 (s, 1H). Elmental analysis calculated for C20H24BrN3O3: C, 55.31; H, 5.57; N, 9.67; Br 18.40. Found: C, 55.22; H, 5.57; N, 9.69; Br 18.18.

EXAMPLE 27

2-[(4-Bromo-2-nitrophenyl)azo]-tert-butyl-4-(2-carbomethoxyethyl)phenol

Added 34.93 g (0.11 mol) of a 40% solution of nitrosylsulfuric acid in sulfuric acid to a rapidly stirred suspension of 4-bromo-2-nitroaniline (23.87 g, 0.11 mol), methyl 3-(3-tert-butyl-4-hydroxyphenyl)propionate (23.63 g, 0.10 mol), concentrated sulfuric acid (3.53 g, 0.036 mol), and Hostapur® SAS93 (1.0 g) in heptane (100 g) and water (50 g) at 5° C. dropwise over 4 hours. The temperature of the reaction mixture is maintained between 2–5° C. during the addition of the nitrosylsulfuric acid. After the addition is complete, the reaction mixture is stirred at 4° C. for 15 minutes and then allowed to warm to ambient temperature. The reaction mixture is stirred overnight at ambient temperature and the resultant precipitate is collected by filtration. The precipitate is washed with water (300 mL) and the solid is dried in vacuo to produce 33.45 grams (72%) of a maroon solid. An analytical sample is prepared by recrystallization from a 1:1 mixture of meta-xylene and methanol (70 mL) to give 12.17 g of fine maroon needles, mp 137–139° C. $^1$H NMR (CDCl$_3$)(499.8494 MHz) δ 1.45 (s, 9H), 2.69 (t, 2H), 2.97 (t, 2H), 3.71 (s, 3H), 7.28 (d, 1H), 7.55 (d, 1H), 7.84 (dd, 1H), 7.91 (d, 1H), 8.24 (d, 1H), 13.40 (s, 1H); MS m/z 463, 465 (M$^+$, M$^+$+2). Calcd. for C20H22BrN3O5: C, 51.74; H, 4.78; N, 9.05. Found: C, 50.33; H, 4.46; N, 9.44.

EXAMPLE 28

(a) 6-Bromo-2-[3-tert-butyl-5-(2-carbomethoxyethyl)-2-hydroxyphenyl]-2H-benzotriazole-1-N-oxide Hydrazine hydrate (1.98 g, 0.062) is added dropwise over 45 minutes to a stirred mixture of 2-[(4-bromo-2-nitrophenyl)azo]-6-tert-butyl-4-(2-carbomethoxyethyl)phenol (11.13 g, 0.024 mol), 5% palladium on carbon (0.5 g), meta-xylene (50 g) and diethylamine (50 g) maintained at 6–8° C. When the addition is complete, the reaction mixture is allowed to warm slowly to room temperature. The reaction mixture is stirred at room temperature for 90 minutes and the catalyst is removed by filtration. The volatiles are removed in vacuo and the residue is recrystallized from methanol (50 mL) to give 7.82 grams (73%) of an orange solid. MS m/z 447, 449 (M$^+$, correct isotope pattern Br); NMR (499.8494 MHz)(CDCl$_3$) δ 1.48 (s, 9H), 2.66 (t, 2H), 2.98 (t, 2H), 3.70 (s, 3H), 7.37 (d, 1H), 7.42 (d, 1H), 7.61 (dd, 1H), 7.75 (d, 1H), 8.05 (d, 1H), 11.58 (s, 1H).

(b) 5-Bromo-2-[3-tert-butyl-5-(2-carbomethoxyethyl)-2-hydroxyphenyl]-2H-benzotriazole Hydrazine hydrate (2.05 g, 0.064) is added dropwise over 115 minutes to a stirred mixture of 6-bromo-2-[3-tert-butyl-5-(2-carbomethoxyethyl)-2-hydroxyphenyl]-2H-benzotriazole-1-N-oxide (7.11 g, 0.016 mol), 5% palladium on carbon (0.5 g), meta-xylene (50 g) and diethylamine (50 g) at 55° C. After the slow addition of hydrazine hydrate is started, the reaction mixture is heated to reflux and held at reflux for 4 hours. The reaction mixture is filtered to remove catalyst and the volatiles are removed in vacuo. Purify the residue by dry-column flash chromatography (80:20 heptane:ethyl acetate eluent) and recrystallization from methanol (35 mL) to give 3.02 grams (44%) of a yellow solid, mp 116–118° C. MS m/z 431, 433 (M+, correct isotope pattern Br); NMR (499.8494 MHz)(CDCl$_3$) δ 1.50 (s, 9H), 2.70 (t, 2H), 3.00 (t, 2H), 3.71 (s, 3H), 7.23 (d, 1H), 7.57 (dd, 1H), 7.83 (d, 1H), 8.12 (d, 1H), 8.13 (d, 1H), 11.57 (s, 1H).

EXAMPLE 29

2-(2-Nitrophenylazo)-6-(1-methyl-1-phenyl-ethyl)-4-(1,1,3,3-tetramethyl-butyl)-phenol Following the general procedure of Example 29, the title compound is prepared.

EXAMPLE 30

Following the general procedure of instant Example 15, the following compounds are prepared:
- 2-(2-nitrophenylazo)-4-(1,1,3,3-tetramethyl-butyl)-phenol;
- 2-(2-nitro-4-trifluoromethylphenylazo)-4-(1,1,3,3-tetramethyl-butyl)-phenol;
- 2,4-bis(3-methyl-butyl)-6-(2-nitrophenylazo)-phenol;
- 3-[3-tert-butyl-4-hydroxy-5-(2-nitro-phenylazo)-phenyl]-propionic acid methyl ester;
- 2,4-bis(1-methyl-1-phenyl-ethyl)-6-(2-nitrophenylazo)-phenol;
- 2,4-di-tert-butyl-6-(4-chloro-2-nitro-phenylazo)-4-methyl-phenol; and
- 2,4-di-tert-butyl-6-(4-chloro-2-nitro-phenylazo)-phenol.

What is claimed is:

1. A process for preparing a compound of formula (I)

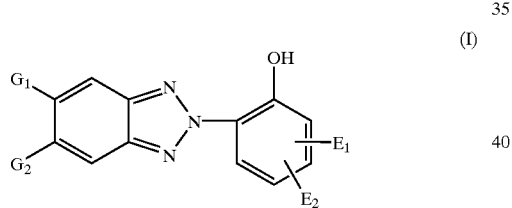

(I)

which process comprises
diazotizing a perfluoroalkyl substituted o-nitroaniline of formula (II)

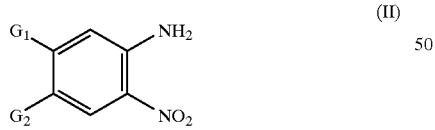

(II)

using concentrated sulfuric acid and an alkali metal nitrite or nitrosylsulfuric acid to form the corresponding diazonium salt of formula (III)

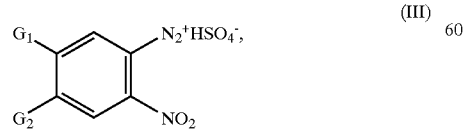

(III)

coupling said diazonium salt with a phenol of formula (IV)

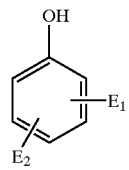

(IV)

to form a monoazobenzene compound of formula (V)

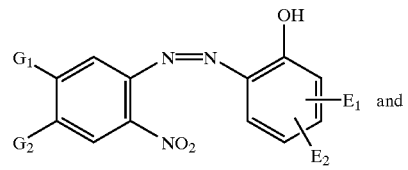

(V) and reducing the monoazobenzene intermediate of formula (V) to the corresponding 2H-benzotriazole compound of formula (I) by conventional reduction means;

wherein $G_1$ is hydrogen or chloro, $G_2$ is perfluoroalkyl of 1 to 12 carbon atoms, $E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_1$ is alkyl of 1 to 24 carbon atoms substituted by one or two hydroxy groups, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —OCOE$_{11}$, —OE$_4$, —NCO, —NHCOE$_{11}$ or —NE$_7$E$_8$, or mixtures thereof, where $E_4$ is straight or branched chain alkyl of 1 to 24 carbon atoms or alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof; or $E_2$ is —(CH$_2$)$_m$—CO—E$_5$;

$E_5$ is OE$_6$ or NE$_7$E$_8$, or $E_5$ is —PO(OE$_{12}$)$_2$, —OSi(E$_{11}$)$_3$ or —OCO—E$_{11}$, or straight or branched chain $C_1$–$C_{24}$alkyl which can be interrupted by —O—, —S— or —NE$_{11}$ and which can be unsubstituted or substituted by —OH or —OCO—E$_{11}$, $C_5$–$C_{12}$cycloalkyl which is unsubstituted or substituted by —OH, straight chain or branched $C_2$–$C_{18}$alkenyl which is unsubstituted or substituted by —OH, $C_7$–$C_{15}$aralkyl, —CH$_2$—CHOH—E$_{13}$ or glycidyl, $E_6$ is hydrogen, straight or branched chain $C_1$–$C_{24}$alkyl which is unsubstituted or substituted by one or more OH, OE$_4$ or NH$_2$ groups, or —OE$_6$ is —(OCH$_2$CH$_2$)$_w$OH or —(OCH$_2$CH$_2$)$_w$OE$_{21}$ where w is 1 to 12 and $E_{21}$ is alkyl of 1 to 12 carbon atoms, $E_7$ and $E_8$ are independently hydrogen, alkyl of 1 to 18 carbon atoms, straight or branched chain alkenyl of 2 to 18 carbon atoms, straight or branched chain $C_3$–$C_{18}$alkyl which is interrupted by —O—, —S— or —$NE_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring, or $E_5$ is —X—$(Z)_p$—Y—$E_{15}$ wherein X is —O— or —N($E_{16}$)—, Y is —O— or —N($E_{17}$)—, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is zero, 1 or 2, p is 1, or p is also zero when X and Y are —N($E_{16}$)— and —N($E_{17}$)—, respectively, $E_{15}$ is a group —CO—C($E_{18}$)=C(H)$E_{19}$ or, when Y is —N($E_{17}$)—, forms together with $E_{17}$ a group —CO—CH=CH—CO—, wherein $E_{18}$ is hydrogen or methyl, and $E_{19}$ is hydrogen, methyl or —CO—X—$E_{20}$, wherein $E_{20}$ is hydrogen, $C_1$–$C_{12}$-alkyl or a group of the formula

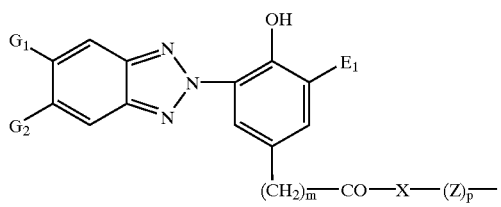

wherein the symbols $E_1$, $G_2$, X, Z, m and p have the meanings defined above, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene, $E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, and $E_{13}$ is H, straight chain or branched $C_1$–$C_{18}$alkyl which is substituted by —PO(O$E_{12}$)$_2$, phenyl which is unsubstituted or substituted by OH, $C_7$–$C_{15}$aralkyl or —CH$_2$O$E_{12}$, with the proviso that when concentrated sulfuric acid and alkali metal nitrite are used, $E_1$ and $E_2$ are alkyl of 1 to 4 carbon atoms, or $E_1$ can also be hydrogen.

2. A process according to claim 1 wherein the alkali metal nitrite is sodium nitrite.

3. A process according to claim 1 wherein nitrosylsulfuric acid is used to diazotize the o-nitroaniline compound of formula (II).

4. A process according to claim 1 for the preparation of a compound of formula (Ia)

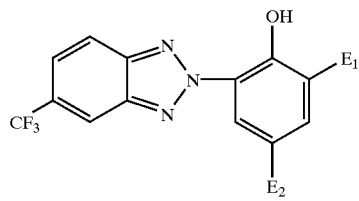

which process comprises diazotizing a substituted o-nitroaniline compound of formula (IIa)

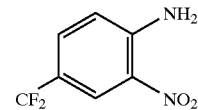

using concentrated sulfuric acid and sodium nitrite or nitrosylsulfuric acid to form the diazonium salt of formula (IIIa)

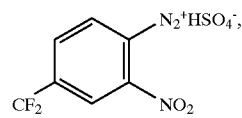

coupling said diazonium salt with a phenol of formula (IVa)

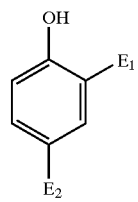

to form the corresponding monoazobenzene compound of formula (Va)

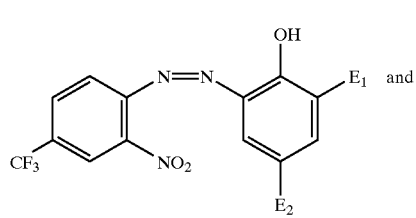

reducing the monoazobenzene intermediate of formula (Va) to the corresponding 2H-benzotriazole compound of formula (Ia) by conventional reduction means;

with the proviso that when concentrated sulfuric acid and alkali metal nitrite are used, $E_1$ and $E_2$ are alkyl of 1 to 4 carbon atoms, or $E_1$ can also be hydrogen.

5. A process according to claim 1 where in the compound of formula (I)

$G_1$ is hydrogen, $G_2$ is —$CF_3$, $E_1$ is phenylalkyl of 7 to 15 carbon atoms, phenyl, or said phenyl or said phenylalkyl substituted on the phenyl ring by one to three alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —$OCOE_{11}$, —$OE_4$, —NCO, —$NH_2$, —$NHCOE_{11}$, —$NHE_4$ or —$N(E_4)_2$, or mixtures thereof, where $E_4$ is straight or branched chain alkyl of 1 to 24 carbon atoms; or said alkyl or said alkenyl interrupted by one or more —O—, —NH— or —$NE_4$ groups or mixtures thereof and which can be unsubstituted or substituted by one or more —OH, —$OE_4$ or —$NH_2$ groups or mixtures thereof; or where in the compound of formula (I)
$G_1$ is hydrogen,
$G_2$ is —$CF_3$,
$E_1$ is hydrogen or straight or branched alkyl of 4 to 24 carbon atoms, and
$E_2$ is as defined above.

6. A process according to claim 1 where in the compound of formula (I)
$G_1$ is hydrogen,
$G_2$ is —$CF_3$,
$E_1$, is hydrogen, straight or branched alkyl of 4 to 24 carbon atoms or phenylalkyl of 7 to 15 carbon atoms,
$E_2$ is $(CH_2)_m$—CO—$E_5$,
$E_5$ is —$OE_6$ or —$NE_7E_8$, or
$E_5$ is —X—$(Z)_p$—Y—$E_{15}$
wherein
X is —O— or —$N(E_{16})$—,
Y is —O— or —$N(E_{17})$—,
Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group,
m is 0, 1, 2 or 3,
p is 1, or p is also zero when X and Y are —$N(E_{16})$— and —$N(E_{17})$—, respectively,
$E_{15}$ is a group —CO—$C(E_{18})$=C(H)$E_{19}$ or, when Y is —$N(E_{17})$—, forms together with $E_{17}$ a group —CO—CH=CH—CO—, wherein $E_{18}$ is hydrogen or methyl, and $E_{19}$ is hydrogen, methyl or —CO—X—$E_{20}$, wherein $E_{20}$ is hydrogen, $C_1$–$C_{12}$-alkyl or a group of the formula

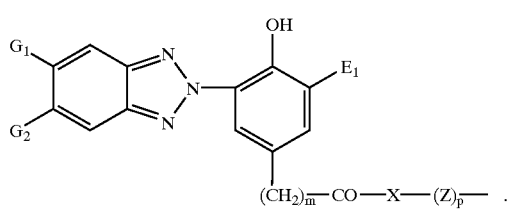

7. A process according to claim 1 where in the compound of formula (I)
$G_1$ is hydrogen, $G_2$ is —$CF_3$, $E_1$ is phenylalkyl of 7 to 15 carbon atoms, phenyl, or said phenyl or said phenylalkyl substituted on the phenyl ring by one to three alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —$OCOE_{11}$, —$NH_2$ or —$NHCOE_{11}$, or mixtures thereof, or said alkyl or said alkenyl interrupted by one or more —O— and which can be unsubstituted or substituted by one or more —OH, or where in the compound of formula (I)
$G_1$ is hydrogen,
$G_2$ is —$CF_3$,
$E_1$ is hydrogen, straight or branched alkyl of 4 to 24 carbon atoms or phenylalkyl of 7 to 15 carbon atoms, and
$E_2$ is as defined above.

8. A process according to claim 1 where in the compound of formula (I)
$G_1$ is hydrogen,
$G_2$ is —$CF_3$,
$E_1$ is hydrogen, straight or branched alkyl of 4 to 24 carbon atoms or phenylalkyl of 7 to 15 carbon atoms,
$E_2$ is $(CH_2)_m$—CO—$E_5$,
$E_5$ is —$OE_6$ or —$NE_7E_8$ where
$E_6$ is hydrogen, straight or branched chain $C_1$–$C_{24}$alkyl which is unsubstituted or substituted by one or more OH groups, or —$OE_6$ is —$(OCH_2CH_2)_w$OH or —$(OCH_2CH_2)_wOE_{21}$ where w is 1 to 12 and $E_{21}$ is alkyl of 1 to 12 carbon atoms, and
$E_7$ and $E_8$ are independently hydrogen, alkyl of 1 to 18 carbon atoms, straight or branched chain $C_3$–$C_{18}$alkyl which is interrupted by —O—, —S— or —$NE_{11}$—, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring.

9. A process according to claim 1 wherein the compound of formula (I) is
(a) 5-trifluoromethyl-2-(2-hydroxy-3-α-cumyl-5-tert-octylphenyl)-2H-benzotriazole;
(b) 5-trifluoromethyl-2-(2-hydroxy-5-tert-octylphenyl)-2H-benzotriazole;
(c) 5-trifluoromethyl-2-(2-hydroxy-3,5-di-tert-octylphenyl)-2H-benzotriazole;
(d) 5-trifluoromethyl-2-[2-hydroxy-5-(2-hydroxyethyl)phenyl]-2H-benzotriazole;
(e) 5-trifluoromethyl-2-(2-hydroxy-3,5-di-α-cumylphenyl)-2H-benzotriazole;
(f) 3-(5-trifluoromethyl-2H-benzotriazol-2-yl)-5-tert-butyl-4-hydroxyhydrocinnamic acid;
(g) methyl 3-(5-trifluoromethyl-2H-benzotriazol-2-yl)-5-tert-butyl-4-hydroxyhydrocinnamate;
(h) isooctyl 3-(5-trifluoromethyl-2H-benzotriazol-2-yl)-5-tert-butyl-4-hydroxyhydrocinnamate;
(i) 5-trifluoromethyl-2-[2-hydroxy-5-(3-hydroxypropyl)phenyl]-2H-benzotriazole;
(j) 5-trifluoromethyl-2-[2-hydroxy-5-(3-acryloyloxypropyl)phenyl]-2H-benzotriazole;

(k) 5-trifluoromethyl-2-[2-hydroxy-5-(3-methacryloyloxypropyl)phenyl]-2H-benzotriazole;
(l) 5-trifluoromethyl-2-[2-hydroxy-5-(3-acrylylaminopropyl)phenyl]-2H-benzotriazole;
(m) 5-trifluoromethyl-2-[2-hydroxy-5-(3-methacrylylaminopropyl)phenyl]-2H-benzotriazole;
(n) 5-trifluoromethyl-2-(2-hydroxy-3-α-cumyl-5-tert-butylphenyl)-2H-benzotriazole;
(o) 5-trifluoromethyl-2-(2-hydroxy-3-α-cumyl-5-nonylphenyl)-2H-benzotriazole;
(p) 5-trifluoromethyl-2-[2-hydroxy-3-α-cumyl-5-(2-hydroxyethyl)phenyl]-2H-benzotriazole;
(q) 5-trifluoromethyl-2-[2-hydroxy-3-α-cumyl-5-(3-hydroxypropyl)phenyl]-2H-benzotriazole;
(r) 5-trifluoromethyl-2-(2-hydroxy-3,5-ditert-amylphenyl)-2H-benzotriazole;
(s) 5-trifluoromethyl-2-(2-hydroxy-3,5-ditert-butylphenyl)-2H-benzotriazole;
(t) 5-trifluoromethyl-2-(2-hydroxy-3-dodecyl-5-methylphenyl)-2H-benzotriazole;
(u) 5-trifluoromethyl-2-[2-hydroxy-3-tert-butyl-5-(3-hydroxypropyl)phenyl)-2H-benzotriazole; or
(v) 5-trifluoromethyl-2-[2-hydroxy-3-tert-butyl-5-(2-hydroxyethyl)phenyl]-2H-benzotriazole.

10. A process according to claim 1 for the preparation of a compound of formula (Ib)

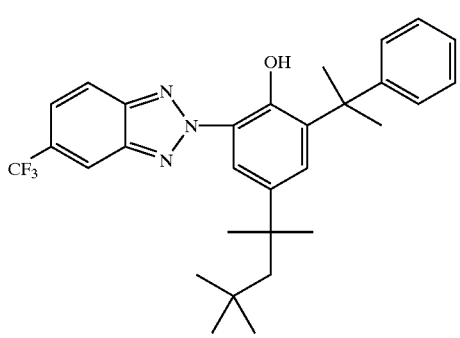
(Ib)

which process comprises diazotizing a substituted o-nitroaniline compound of formula (IIa)

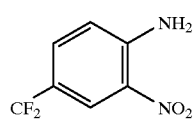
(IIa)

using nitrosylsulfuric acid to form the diazonium salt of formula (IIIa)

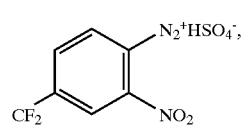
(IIIa)

coupling said diazonium salt with a phenol of formula (IVb)

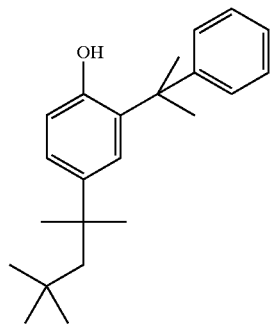
(IVb)

to form the corresponding monoazobenzene compound of formula (Vb)

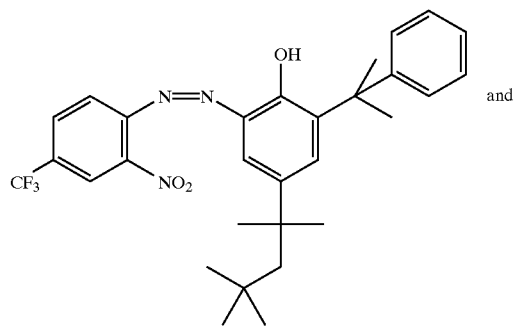
(Vb)

and reducing the monoazobenzene intermediate of formula (Vb) to the corresponding 2H-benzotriazole compound of formula (Ib) by conventional reduction means.

11. A process according to claim 1 for the preparation of a compound of formula (Ic)

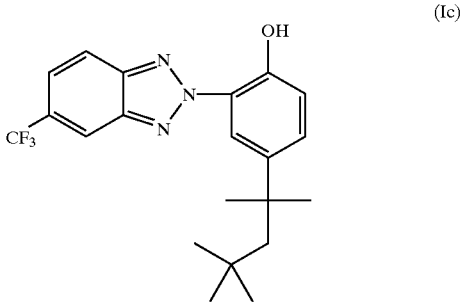
(Ic)

which process comprises diazotizing a substituted o-nitroaniline compound of formula (IIa)

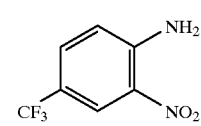
(IIa)

using nitrosylsulfuric acid to form the diazonium salt of formula (IIIa)

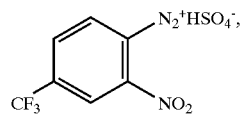

coupling said diazonium salt with a phenol of formula (IVc)

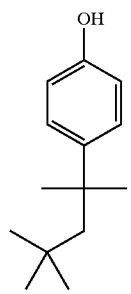

to form the corresponding monoazobenzene compound of formula (Vc)

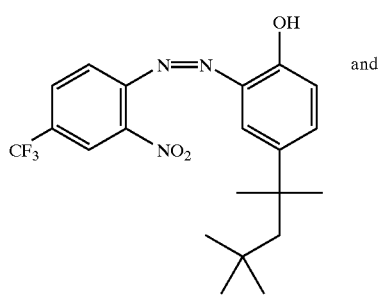

reducing the monoazobenzene intermediate of formula (Vc) to the corresponding 2H-benzotriazole compound of formula (Ic) by conventional reduction means.

12. A process according to claim 1 where in the process for making the diazonium salts using a perfluoroalkyl substituted o-nitroaniline (i.e. 4-trifluoromethyl-2-nitroaniline, $CF_3$-ONA), sulfuric acid and an aqueous alkali metal nitrite solution,
   a. the molar ratio of $CF_3$-ONA:sulfuric acid is 1:10 to 1:1;
   b. the molar ratio of $CF_3$-ONA:sodium nitrite is 1:1 to 1:4; and
   c. the temperature used for this reaction is from $-30°$ C. to $50°$ C.

13. A process according to claim 12 wherein
   a. the molar ratio of $CF_3$-ONA:sulfuric acid is 1:5 to 1:1;
   b. the molar ratio of $CF_3$-ONA:sodium nitrite is 1:1 to 1:2; and
   c. the temperature used for this reaction is from $-20°$ C. to $20°$ C.

14. A process according to claim 13 wherein
   a. the molar ratio of $CF_3$-ONA:sulfuric acid is 1:2–3.5;
   b. the molar ratio of $CF_3$-ONA:sodium nitrite is 1:1; and
   c. the temperature used for this reaction is from $-10°$ C. to $5°$ C.

15. A process according to claim 1 where in the process for making the diazonium salts using a perfluoroalkyl substituted o-nitroaniline (i.e. 4-trifluoromethyl-2-nitroaniline, $CF_3$-ONA) and nitrosylsulfuric acid,
   a. the molar ratio of $CF_3$-ONA:nitrosylsulfuric acid is 1:1 to 1:2;
   b. the molar ratio of $CF_3$-ONA:sulfuric acid is 1:1 to 1:10, and
   c. the temperature used for this reaction is from $-30°$ C. to $50°$ C.

16. A process according to claim 15 wherein
   a. the molar ratio of $CF_3$-ONA:nitrosylsulfuric acid is 1:1 to 1:1.2;
   b. the molar ratio of $CF_3$-ONA:sulfuric acid is 1:2 to 1:7; and
   c. the temperature used for this reaction is from $-20°$ C. to $40°$ C.

17. A process according to claim 16 wherein
   a. the molar ratio of $CF_3$-ONA:nitrosylsulfuric acid is 1:1;
   b. the molar ratio of $CF_3$-ONA:sulfuric acid is 1:2 to 1:5; and
   c. the temperature used for this reaction is from $0°$ C. to $25°$ C.

18. A process according to claim 1 wherein the monoazobenzene intermediate of formula (V) is prepared in a solvent containing a surface active modifier at a temperature of $-30°$ C. to $75°$ C.

19. A process according to claim 18 wherein the temperature is $-20°$ C. to $50°$ C.

20. A process according to claim 19 wherein the temperature is $-10°$ C. to $35°$ C.

21. A process according to claim 18 wherein the solvent is water, an aromatic hydrocarbon, an aliphatic hydrocarbon or a mixture thereof.

22. A process according to claim 21 wherein the solvent is water, toluene, o-xylene, m-xylene, p-xylene, a mixture of said xylenes, mesitylene, pseudocumene, hexane, heptane, octane, nonane or a mixture thereof.

23. A process according to claim 22 wherein the solvent is water, toluene, o-xylene, m-xylene, p-xylene, a mixture of said xylenes, heptane or a mixture thereof.

24. A process according to claim 18 wherein the surface active modifier is selected from the group consisting of emulsifying agents, surfactants, phase transfer agents and dispersants.

25. A process according to claim 24 wherein the surface active modifier is HOSTAPUR® SAS93 (Hoechst) or PETROSUL® M60 (Penreco).

26. A process according to claim 1 wherein the molar ratio of diazonium salt:phenol is 2:1 to 1:2.

27. A process according to claim 26 wherein the molar ratio of diazonium salt:phenol is 1.5:1 to 1:1.5.

28. A process according to claim 27 wherein the molar ratio of diazonium salt:phenol is 1:1.

* * * * *